(12) United States Patent
Firestein-Miller

(10) Patent No.: US 7,888,461 B2
(45) Date of Patent: Feb. 15, 2011

(54) SNAPIN AND METHODS FOR REGULATION OF MICROTUBULE ASSEMBLY AND DENDRITE GROWTH AND BRANCHING

(76) Inventor: Bonnie L. Firestein-Miller, 300 E. Mountain Rd., Hillsborough, NJ (US) 08844

( * ) Notice: Subject to any disclaimer, the term of this patent is extended or adjusted under 35 U.S.C. 154(b) by 107 days.

(21) Appl. No.: 11/887,687

(22) PCT Filed: Apr. 4, 2006

(86) PCT No.: PCT/US2006/013218

§ 371 (c)(1), (2), (4) Date: Oct. 2, 2007

(87) PCT Pub. No.: WO2006/132701

PCT Pub. Date: Dec. 14, 2006

(65) Prior Publication Data

US 2009/0053745 A1    Feb. 26, 2009

Related U.S. Application Data

(60) Provisional application No. 60/667,774, filed on Apr. 4, 2005.

(51) Int. Cl.
*A61K 38/00* (2006.01)
*A61K 39/00* (2006.01)
*G01K 33/53* (2006.01)
*G01K 33/567* (2006.01)

(52) U.S. Cl. .................... 530/324; 530/300; 424/184.1; 424/185.1; 435/7.1; 435/7.21; 436/501

(58) Field of Classification Search ....................... None
See application file for complete search history.

(56) References Cited

FOREIGN PATENT DOCUMENTS

WO    WO0146256    *    6/2001
WO    WO02086122 A2 *  10/2002

* cited by examiner

*Primary Examiner*—Olga N Chernyshev
(74) *Attorney, Agent, or Firm*—Fox Rothschild LLP; Gerard P. Norton

(57) ABSTRACT

Fragments of snapin important for interaction with cypin and thus regulating microtubule assembly are provided. Also provided are methods of use of said fragments and kits to facilitate said methods.

11 Claims, 9 Drawing Sheets

α-Snapin

A.

B.

C.

SNAPIN AND METHODS FOR REGULATION OF MICROTUBULE ASSEMBLY AND DENDRITE GROWTH AND BRANCHING

CROSS-REFERENCE TO RELATED APPLICATIONS

This application claims priority to U.S. provisional patent application Ser. No. 60/667,774, filed Apr. 4, 2005, which is herein incorporated by reference.

GOVERNMENT SUPPORT

This invention was made with U.S. Government funds (NSF IBN 0234206). Therefore, the Government may have rights in this invention.

FIELD OF THE INVENTION

The present invention generally relates to the structure, function and uses of a protein and fragments thereof, alone and in combination, involved in the regulation of nerve cell activity and morphology, which affects learning and memory disorders.

BACKGROUND

The establishment of dendrite morphology is crucial for normal neuronal communication in the brain. This process includes both the spatial and functional assembly of signal transduction machinery at synaptic sites and precise patterning of dendrites and their branches. Branching patterns, the relationship between the primary dendrites arising from the cell body and the secondary dendrites arising from primary dendrites, appear to be cell-type specific and play a role in determining how information is received and processed by a neuron. The amount of branches that a dendrite, or input center of a neuron, contains is thought to be directly related to learning and memory. In many learning disorders, such as autism, Rett syndrome, Down syndrome, Fetal Alcohol syndrome and Alzheimer's disease, patients show a reduced number of dendrite branches.

When there is an abnormal decrease in the number of dendrite branches on a neuron, the neuron cannot receive appropriate information, and hence disruption of proper signaling networks results (Vetter et al., 2001; Schaefer et al., 2003). Thus, there is a great interest in understanding how the number of dendrites produced by a neuron is determined.

A first step of elucidating the mechanism by which dendrite number is regulated is to identify the players in this process. Dendrite arbors are shaped by an interplay between intrinsic and extrinsic factors. Some of the known intrinsic factors are calcium/calmodulin-dependent protein kinase II (Fink et al., 2003), the small GTPases RhoA, Rac 1, and Cdc42 (Threadgill et al., 1997; Ruchhoeft et al., 1999; Li et al., 2000), novel genes identified in *Drosophila* (Gao et al., 1999; Moore et al., 2002; Grueber et al., 2003; Yu and Malenka, 2003; Emoto et al., 2004), β-catenin (Yu and Malenka, 2003), Dishevelled (Rosso et al., 2005), a calcium-responsive transactivator called CREST (Aizawa et al., 2004), and cypin (cytosolic PSD-95 interactor; (Firestein et al., 1999; Akum et al., 2004). The external factors comprise a long list and include neurotrophins (McAllister et al., 1995; McAllister et al., 1997; Baker et al., 1998; Horch et al., 1999; Lom and Cohen-Cory, 1999), electrical activity (McAllister et al., 1996; Cambiasso et al., 2000; Vaillant et al., 2002; Yu and Malenka, 2003) and estrogen (Cambiasso et al., 2000; Audesirk et al., 2003, 2003; Sakamoto et al., 2003; Dominguez et al., 2004; Nathan et al., 2004). As of yet, there have been only a small number of studies that examine how the extracellular and intrinsic factors are linked to determine dendrite morphology. The inventors have recently reported that cypin protein levels are increased in response to extracellular factors, such as KCl and NGF, that increase dendrite number (Akum et al., 2004).

Further, the inventors have found that cypin acts to increase dendrite number by binding to tubulin heterodimers and promoting microtubule assembly (Akum et al., 2004). The collapsin response mediator protein (CRMP) homology domain is responsible for this activity (Akum et al., 2004).

Since the understanding of the pathways by which dendrite number is regulated is crucial for proper diagnosis and treatment of learning disorders, such as autism, Rett syndrome, Down syndrome, Fetal Alcohol syndrome and Alzheimer's disease, it is necessary to identify proteins that interact with cypin and act to regulate dendrite number as part of a cypin protein complex.

SUMMARY OF INVENTION

In one aspect, the invention provides an isolated peptide derived from the full length snapin between about 50 and about 90 consecutive amino acids in length, which comprises an amino acid sequence substantially identical to the coiled coil domain of snapin, wherein said amino acid sequence substantially identical to the coiled coil domain is capable of binding at least a portion of cypin. In one embodiment, the invention comprises the peptide described above, wherein at least one amino acid located upstream of the amino-terminus of the amino acid sequence substantially identical to the coiled coil domain is capable of being phosphorylated.

In another aspect, the invention provides an isolated nucleic acid sequence comprising a nucleic acid sequence encoding a peptide substantially identical to the peptides described above.

In another aspect, the invention provides a vector comprising the nucleic acid sequence described above.

In another aspect, the invention provides host cells comprising a vector described above.

In another aspect, the invention provides a method of altering binding between at least a portion of cypin and at least a portion of tubulin comprising providing a sample containing at least the portion of cypin and at least the portion of tubulin; and adding at least a portion of snapin to the sample.

In another aspect, the invention provides a screening method comprising: providing a sample containing at least a portion of cypin and at least a portion of snapin; adding a test compound to at least a first portion of the sample; and comparing at least one parameter from at least the first portion of the sample with the at least one parameter from at least a second portion of the sample, wherein at least the second portion of the sample does not include the test compound. In another aspect, the invention provides a screening method comprising providing a sample containing at least a portion of cypin and at least a portion of snapin; adding at least a portion of tubulin to the sample; adding a test compound to at least a first portion of the sample; and comparing at least one parameter from at least the first portion of the sample with the at least one parameter from at least a second portion of the sample, wherein at least the second portion of the sample does not include the test compound.

A magnitude of a difference between the at least one parameter from at least the first portion of the sample and the at least one parameter from at least the second portion of the sample is an indication of, inter alia, the test compound's ability to alter a binding between snapin and cypin, a number of primary processes in a cell, a probability of branching in a cell or a microtubule assembly in a cell or cell-free system. In another aspect, the invention provides a kit comprising at least a portion of cypin, at least the portion of cypin being capable of binding at least the portion of tubulin; and at least a portion of snapin, at least the portion of snapin being capable of binding at least the portion of cypin.

In another aspect, the instant invention provides a screening method comprising: providing a sample comprising at least a portion of snapin and adding a test compound to at least a first portion of the sample, and determining an amount of at least the portion of snapin which is phosphorylated. The magnitude of a difference between the amount of at least the portion of snapin which is phosphorylated in at least the first portion of the sample and the amount of at least the portion of snapin which is phosphorylated in at least the second portion of the sample, wherein at least the second portion of the sample does not include the test compound, is an indication of, inter alia, the test compound's ability to alter a binding between snapin and cypin, a number of primary processes in a cell, a probability of branching in a cell or a microtubule assembly in a cell or cell-free system.

In yet another aspect, the invention provides a method for use in the diagnosis of a cognitive disorder in a subject comprising detecting a test amount of a snapin gene product in a sample from the subject; and comparing the test amount with a normal amount of snapin gene product in a control sample, whereby a finding that the test amount is outside of the normal range for the snapin gene product provides a positive indication in the diagnosis of a cognitive disorder. In another embodiment, the method comprises: detecting a test amount of a phosphorylated snapin protein in a sample from the subject and comparing the test amount with a normal amount of the phosphorylated snapin protein in a control sample, whereby the amount in the test sample outside of the control range provides a positive indication in the diagnosis of a cognitive disorder.

In another aspect, the invention provides a method for use in the prognosis of a cognitive disorder in a subject comprising the steps of: detecting a test amount of a snapin gene product in a sample from the subject; and comparing the test amount with prognostic amounts of the snapin gene product in control samples, whereby a comparison of the test amount with the prognostic amounts provides an indication of the prognosis of cognitive disorder. In another embodiment, the method comprises: detecting a test amount of a phosphorylated snapin protein in a sample from the subject and comparing the test amount with a normal amount of the phosphorylated snapin protein in a control sample, whereby a comparison of the test amount with the normal amounts provides an indication of the prognosis of cognitive disorder.

In yet another aspect, the invention provides a method for use in monitoring the course of a cognitive disorder in a subject comprising the steps of: detecting a first test amount of a snapin gene product in a sample from the subject at a first time; detecting a second test amount of the snapin gene product in a sample from the subject at a second, later time; and comparing the first test amount and the second test amount, whereby the normal range of the snapin gene product amount closer to the snapin gene product measured at the second time than to the amount of the snapin gene product measured at the first time indicates that the disorder has improved; and the normal range of the snapin gene product amount closer to the snapin gene product measured at the first time than to the amount of the snapin gene product measured at the second time indicates that the disorder has progressed. In another embodiment, the method comprises: detecting a first test amount of a phosphorylated snapin protein in a sample from the subject at a first time; detecting a second test amount of the phosphorylated snapin protein in a sample from the subject at a second, later time; and comparing the first test amount and the second test amount, whereby the normal range of the phosphorylated snapin protein amount closer to the phosphorylated snapin protein measured at the second time than to the amount of the phosphorylated snapin protein measured at the first time indicates that the disorder has improved; and the normal range of the phosphorylated snapin protein amount closer to the phosphorylated snapin protein measured at the first time than to the amount of the phosphorylated snapin protein measured at the second time indicates that the disorder has progressed.

In yet another aspect, the invention provides a method for assessing the efficacy of a treatment for a cognitive disorder in a subject comprising the steps of: detecting a first test amount of a snapin gene product in a sample from the subject prior to treatment; detecting a second test amount of the snapin gene product in a sample from the subject after treatment; and comparing the first test amount and the second test amount, whereby the normal range of the snapin gene product amount closer to the snapin gene product measured at the second time than to the amount of the snapin gene product measured at the first time indicates that the treatment is efficient; and the normal range of the snapin gene product amount closer to the snapin gene product measured at the first time than to the amount of the snapin gene product measured at the second time indicates that the treatment is not efficient. In another embodiment, the method comprises: detecting a first test amount of a phosphorylated snapin protein in a sample from the subject at a first time; detecting a second test amount of the phosphorylated snapin protein in a sample from the subject at a second, later time; and comparing the first test amount and the second test amount, whereby the normal range of the phosphorylated snapin protein amount closer to the phosphorylated snapin protein measured at the second time than to the amount of the phosphorylated snapin protein measured at the first time indicates that the treatment is efficient; and the normal range of the phosphorylated snapin protein amount closer to the phosphorylated snapin protein measured at the first time than to the amount of the phosphorylated snapin protein measured at the second time indicates that the treatment is not efficient.

In yet another aspect, the invention provides an antibody for detection of at least a portion of snapin polypeptide.

In yet another aspect, the invention provides a kit comprising the antibody for detection of at least a portion of snapin polypeptide, and a set of instructions.

DETAILED DESCRIPTION

Figure 1:
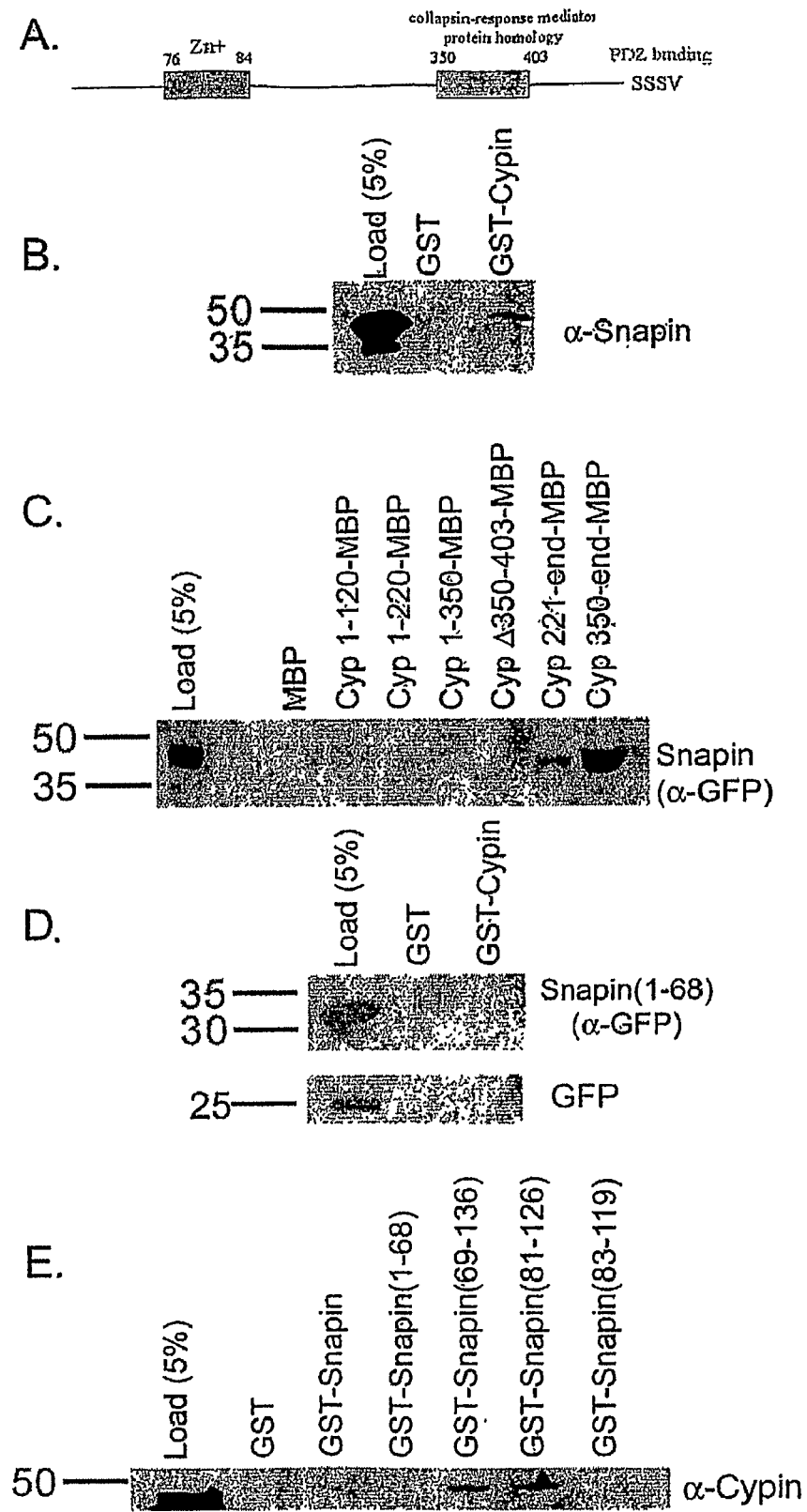
FIG. 1 illustrates the results of experiments demonstrating that cypin binds snapin in vitro and that the CRMP domain of cypin (amino acids 350-403) and coiled coil domain of snapin (amino acids 81-126) are important for the binding.

The present invention results from the unexpected discovery of several physiological functions for snapin that has not heretofore been described. This discovery has permitted the development of methods of using snapin in assays for diagnosing and monitoring cognitive disorders, as well as assays for identifying and developing test compounds to prognose, diagnose, monitor, and treat these disorders.

DEFINITIONS

To aid in the understanding of the invention, the following non-limiting definitions are provided: The term "sample" includes both cells and cell-free systems. Further, the term "sample" includes cells or cell-tree solutions, wherein at least one substance is immobilized, such as, for example, attached to a column or to a well of, for example, a testing plate.

The term "compound" refers to both single substance, such as, for example, a protein, a small molecule, a nucleic acid sequence and a cocktail of substances, such as, for example, a combination of a protein and a small molecule.

The phrase "at least a portion of" an entity includes the whole entity. Accordingly, at least a portion of an amino acid or a nucleic acid sequence includes the whole amino acid or nucleic acid sequence.

The phrase "primary processes" refers to processes stemming out of the cell body.

The term "branching" refers to a formation of processes not stemming out of the cell body, but instead, to processes stemming out of stemming out of other processes, e.g., primary processes.

The terms "quantifying," "determining quantity," "determining an amount," or determining a number" of a parameter includes determining both absolute values (e.g., meters, kilograms) and relative values (e.g., relative light units or ratios compared to control values).

The term "diagnostic" or "diagnosing" means identifying the presence or absence of a pathologic condition.

The term "prognostic" or "prognosing" means predicting the probable development and/or severity of a pathologic condition.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "patient" includes a living or cultured system upon which the methods and/or kits of the current invention is used. The term includes, without limitation, humans.

The term "upstream" refers to a location closer to the N-terminus of a protein, peptide, or amino acid sequence, or closer to the 5'-end of a nucleic acid sequence.

The term "substantially identical" refers to at least about 70% structural identicalness between two or more entities, such as, for example, two or more amino acid sequences or two or more nucleic acid sequences.

A person of ordinary skill in the art will appreciate that detecting the test amount of the phosphorylated snapin protein can be done directly or indirectly. For example, determining the ratios of:

a) the amount of phosphorylated snapin protein or at least a portion thereof to the total amount of snapin protein or at least the portion thereof;

b) the total amount of snapin protein or at least a portion thereof to the amount of phosphorylated snapin protein or at least the portion thereof;

c) the amount of unphosphorylated snapin protein or at least a portion thereof to the total amount of snapin protein or at least the portion thereof;

d) the total amount of snapin protein or at least a portion thereof to the amount of phosphorylated snapin protein or at least the portion thereof;

e) the amount of phosphorylated snapin protein or at least a portion thereof to the amount of unphosphorylated snapin protein or at least the portion thereof; and f) the amount of unphosphorylated snapin protein or at least a portion thereof to the amount of phosphorylated snapin protein or at least the portion thereof, can all be used for the methods of this invention. Accordingly, determining the ratios above are included within the meaning of the phrase "determining the amount of a phosphorylated snapin protein."

In one aspect, the invention provides at least a portion of snapin peptide sequences important for binding with at least a portion of cypin.

In one embodiment, at least the portion of snapin peptide comprises an isolated peptide derived from the full length snapin peptide between about 50 and about 90 consecutive amino acids in length, which comprises an amino acid sequence substantially identical to the coiled coil domain of snapin, wherein said amino acid sequence substantially identical to the coiled coil domain of snapin is capable of binding at least the portion of cypin.

It has been recently found that the coiled coil domain important for binding to at least the portion of cypin is located between amino acids 81 and 126 of the full length snapin amino acid sequence. The inventors found that the peptide fragment of snapin comprising amino acids 69-136 of snapin is important for binding with at least the portion of cypin. It has also been found that serine in position 50 of the full amino acid sequence of snapin can be phosphorylated by such compounds as, for example, PKA, and that the phosphorylation of serine at this position alters the dynamics of binding snapin to cypin. Accordingly, in one embodiment, the invention further comprises the isolated peptide derived from the full length snapin peptide between about 50 and about 90 consecutive amino acids in length, which comprises an amino acid sequence substantially identical to the coiled coil domain of snapin, wherein said amino acid sequence substantially identical to the coiled coil domain of snapin is capable of binding at least the portion of cypin, wherein at least one amino acid, preferably located about 33 positions upstream of the N-terminus of the coiled coil domain, can be phosphorylated. Preferably, phosphorylation of the at least one amino acid alters an ability of the peptide to bind at least the portion of cypin. It has been long known that serine, tyrosine, and threonine possess hydroxyl groups, which can be phosphorylated. Accordingly, any of these amino acids can be used as the at least one amino acid. Preferably, the at least one amino acid is serine.

In another embodiment, the invention comprises an isolated nucleic acid sequence comprising a nucleic acid sequence encoding a peptide substantially identical to the peptide described above. A person of ordinary skill in the art will understand that because of the degeneracy of the genetic code, a large number of nucleic acid sequences can be generated in accordance with this invention.

A person or ordinary skill in the art will further understand that the nucleic acid sequences of this invention may be subcloned into a vector, such as, for example, a viral vector or a plasmid. The suitable non-limiting examples of vectors and subcloning methods are described in, for example, Sambrook and Russel, *Molecular Cloning: A Laboratory Manual* ($3^{rd}$ Edition), Cold Spring Harbor Press, NY, 2000, contents of which are incorporated in this disclosure.

Further, a person of ordinary skill in the art will appreciate that the nucleic acid sequences can be introduced into cells of choice, such as, for example, neurons. Methods of introducing exogenous nucleic acid sequences are also described in Sambrook and Russel, *Molecular Cloning: A Laboratory Manual* ($3^{rd}$ Edition), Cold Spring Harbor Press, NY, 2000. These methods include, without limitation, physical transfer techniques, such as, for example, microinjection or electroporation; transfections, such as, for example, calcium phosphate transfections; membrane fusion transfer, using, for example, liposomes; and viral transfer, such as, for example, the transfer using DNA or retroviral vectors.

The methods of making the peptides and nucleic acid sequences of this invention are well-known in the art.

Any snapin can be used in the methods of the present invention. The amino acid sequences of various snapin polypeptides are publicly available from Genbank and include human (Acc. No. NP_036569), mouse (Acc. No. NP_598615), and *Drosophila* (Acc. No. NP_722835). Snapin can be isolated from natural sources, produced by recombinant methods, or produced through in vitro protein synthesis. Thus, the present invention does not require that snapin be naturally occurring.

The peptides of the instant invention may differ from the naturally occurring protein in terms of one or more amino acid substitutions, deletions, additions, or rearrangements. For example, functionally equivalent amino acid residues may be substituted for residues within the sequence resulting in a change of sequence. Such substitutes may be selected from other members of the class to which the amino acid belongs: e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic acid and glutamic acid.

Snapin can be purified or partially purified from various tissues (preferably mammalian; more preferably human), including, without limitation, brain, bone, cervix, colon, eye, kidney, liver, lung, mammary gland, muscle, ovary, pancreas, placenta, small intestine, stomach, tongue, testis, uterus, and adipocytes, using known purification processes such as gel filtration and ion exchange chromatography. Purification may also include affinity chromatography with agents known to bind snapin (e.g., cypin or at least a portion thereof or anti-snapin antibodies.). These purification processes may also be used to purify snapin (or at least a portion thereof) from recombinant sources.

Once purified, the cleavage of the snapin into fragments of amino acid residues can be achieved using proteolytic enzymes such as thrombin or clostridiopeptidase B (clostripain). The exact time required for proteolysis varies with each snapin preparation and markedly depends upon the batch of clostripain used. Therefore, the optimum time for a single cleavage must be determined for each combination of clostripain batch and snapin used. The snapin fragments resulting from either thrombin or clostripain proteolysis may be further cleaved by digestion with trypsin, which cleaves on the carboxy terminus of lysine or arginine residues.

The sequence of snapin derived from proteolytic digestion may be identified using the Edman degradation method of protein sequencing. In addition, sequence analysis of snapin may be accelerated by using an automated liquid phase amino acid sequenator, thereby allowing for the analysis of picomolar quantities of snapin containing up to 50 amino acid residues in length.

The production of snapin can also be achieved by recombinant DNA technology. Nucleic acid sequences encoding snapin (or at least the portion thereof) can be produced using methods well known in the art, including, for example, chemical synthesis and PCR. Nucleic acid sequences encoding snapin polypeptides are publicly available from Genbank and include human (Acc. No. NM_130811), mouse (Acc. No. NM_133854), and rat (Acc. No. NM_001025648). Due to the degeneracy of the genetic code, many different nucleotide sequences can encode the snapin polypetides. The codons can be selected for optimal expression in prokaryotic or eukaryotic systems. Homologous sequences (both paralogues and orthologues) can also be used so long as they retain at least the partial structure and/or activity of snapin. Methods for identifying homologous nucleic acid and amino acid sequences are well known in the art and include both hybridization-based and bioinformatics-based approaches (see Baxevanis and Ouellette, *Bicinformatics, A Practical Guide to the Analysis of Genes and Proteins* (2001)).

In another aspect, the current disclosure provides antibodies binding at least the portion of snapin to be used in the kits and methods of the present invention. The antibodies can be produced by methods well known to those skilled in the art. For example, monoclonal antibodies to at least the portion of snapin can be produced by generation of hybridomas in accordance with known methods. Hybridomas formed in this manner are then screened using standard methods, such as ELISA, to identify one or more hybridomas that produce an antibody that specifically binds to at least the portion of snapin.

As an alternative to preparing monoclonal antibody-secreting hybridomas, a monoclonal antibody to snapin, or a fragment thereof, may be identified and isolated by screening a recombinant combinatorial immunoglobulin library (e.g., an antibody phage display library) to thereby isolate immunoglobulin library members that bind to at least the portion of snapin. Kits for generating and screening phage display libraries are commercially available from, e.g., Dyax Corp. (Cambridge, Mass.) and Maxim Biotech (South San Francisco, Calif.). Additionally, examples of methods and reagents particularly amenable for use in generating and screening antibody display libraries can be found in the literature.

Polyclonal sera and antibodies may be produced by immunizing a suitable subject, such as a rabbit, with at least the portion of snapin (preferably mammalian; more preferably human). The antibody titer in the immunized subject may be monitored over time by standard techniques, such as with ELISA, using immobilized marker protein. If desired, the antibody molecules directed against at least the portion of snapin may be isolated from the subject or culture media and further purified by well-known techniques, such as protein A chromatography, to obtain an IgG fraction, or by affinity chromatography, similar to methods described in Firestein et al., Neuron 24:659 (1999).

Fragments of antibodies to at least the portion of snapin may be produced by cleavage of the antibodies in accordance with methods well known in the art. For example, immunologically active F(ab') and F(ab')$_2$ fragments may be generated by treating the antibodies with an enzyme such as pepsin. Additionally, chimeric, humanized, and single-chain antibodies to at least the portion of snapin, comprising both human and nonhuman portions, may be produced using standard recombinant DNA techniques. Humanized antibodies to at least the portion of snapin may also be produced using transgenic mice that are incapable of expressing endogenous immunoglobulin heavy and light chain genes, but which can express human heavy and light chain genes.

Screening Tests

In another aspect, the present invention provides methods of screening test compounds for treatment of diseases associated with abnormal microtubule assembly, abnormal number of primary processes, or an abnormal probability of branching.

In one embodiment, the invention provides a screening method comprising providing a sample containing at least a portion of cypin and at least a portion of snapin; adding a test compound to at least a first portion of the sample; and comparing at least one parameter from at least the first portion of the sample with the at least one parameter from at least a second portion of the sample, wherein at least the second portion of the sample does not include the test compound.

A person of ordinary skill in the art will appreciate that different variables can be used as the at least one parameter in different embodiments of the current invention. Suitable non-limiting examples of the at least one parameter are: a) an amount of a complex between at least the portion of cypin and at least the portion of snapin, b) an amount of at least the portion of snapin not bound to at least the portion of cypin, c) an amount of at least the portion of cypin not bound to at least the portion of snapin, and any combination thereof.

In another embodiment, the method comprises providing a sample containing at least a portion of cypin and at least a portion of snapin; adding at least a portion of tubulin to the sample; adding a test compound to at least a first portion of the sample; and comparing at least one parameter from at least the first portion of the sample with the at least one parameter from at least a second portion of the sample, wherein at least the second portion of the sample does not include the test compound.

A person of ordinary skill in the art will appreciate that different variables can be used as the at least one parameter in different embodiments of the current invention. Suitable non-limiting examples of the at least one parameter are: a) an amount of a complex between at least the portion of cypin and at least the portion of snapin, b) an amount of at least the portion of snapin not bound to at least the portion of cypin, c) an amount of at least the portion of cypin not bound to at least the portion of snapin, d) an amount of a complex between at least the portion of cypin and at least the portion of tubulin, e) an amount of at least the portion of tubulin not bound to at least the portion of cypin, and any combination thereof.

In one embodiment of this method, at least a portion of cypin is used. A person of ordinary skill in the art will appreciate that only a portion of cypin is necessary to practice the method of the current invention as long as at least the portion of cypin is capable of binding at least the portion of tubulin or at least the portion of snapin. In one embodiment, the portion of cypin includes the CRMP homology domain, corresponding to amino acids 350-403 of cypin polypeptide. Alternatively, the whole amino acid sequence of cypin can be used. The at least the portion of cypin may be obtained according to the methods described above or in accordance with co-pending U.S. patent application Ser. No. 11/033,909.

A person of ordinary skill in the art will further appreciate that the whole sequence of tubulin is not necessary for the practice of this invention as long as at least a portion of tubulin is capable of forming polymers, including dimers) and capable of binding at least the portion of cypin.

Similarly, a person of ordinary skill in the art will appreciate that only a portion of snapin is necessary to practice the method of the current invention as long as the portion of snapin is capable of binding cypin. In one embodiment, the portion of snapin includes the coiled coil domain, corresponding to amino acids 81-126 of snapin polypeptide. Alternatively, the carboxyl terminal corresponding to amino acids 69-136 or even the whole amino acid sequence of snapin can be used.

In a different embodiment of the invention, at least the portion of snapin comprising not only the coiled coil domain or a part thereof necessary for binding to at least the portion of cypin, but also an upstream amino acid sequence, wherein at least one amino acid, preferably located about 33 positions upstream of the N-terminus of the coiled coil domain, can be phosphorylated. Preferably, phosphorylation of the at least one amino acid alters an ability of the peptide to bind at least the portion of cypin. It has been long known that serine, tyrosine, and threonine include hydroxyl groups which can be phosphorylated. Accordingly, any of these amino acids can be used as the at least one amino acid. Preferably, the at least one amino acid is serine.

Suitable test compounds include proteins, nucleic acids, and small molecules, both organic and inorganic. For example, suitable nucleic acid sequences include, without limitation, siRNA for snapin or vectors capable of snapin overexpression. Proteins may include antibodies, which recognize snapin or at least the portion thereof, or, in different embodiments, proteins involved in intracellular signaling cascades, such as, for example, PKA or proteins regulated by PKA.

Further, test compounds may include combinations of these compounds in different embodiments of the invention. As described above, it has been shown that phosphorylation of snapin in position 50 decreases its binding to cypin. Accordingly, a suitable non-limiting example of the at least the portion of snapin would be the full amino acid sequence of snapin and the test compound may comprise a cocktail of a phosphorylating enzyme and a source of the phosphate, such as, for example, ATP or GTP.

Sample selection ultimately depends on the nature of the test compound. If the test compound requires cell machinery for its proper effect on the expression or the activity of snapin, the appropriate sample comprises cells. An example of the test compound suitable for the use in the sample comprising cells is a nucleic acid encoding a protein affecting the expression or the activity of snapin. On the other hand, if the cell machinery is not required for the proper action of the test compound, cell-free systems can be used. Suitable non-limiting examples of the suitable test compounds in this embodiment are small molecules, antibodies or enzymes.

Upon comparing the at least one parameter from at least the first portion of the sample with the at least one parameter from either at least a second portion of the sample, which does not include the test compound, or with pre-set standards (i.e. pre-calibrated standard curve), a user of any of the methods described above may make predictions about and select the appropriate test compound based on the test compound's ability to alter a binding between snapin and cypin, to alter a number of primary processes in a cell, to alter a probability of branching in a cell, and/or to alter a microtubule assembly in a cell or cell-free system.

For example, an increase in the amount of at least the portion of cypin bound to at least the portion of snapin indicates an ability of the test compound to inhibit a microtubule assembly in a cell, decrease a number of primary processes in the cell, increase a probability of branching in the cell, and increase a binding between snapin and cypin. A decrease in the amount of at least the portion of cypin bound to at least the portion of snapin indicates an ability of the test compound to decrease a quantity of primary processes in a cell, induce microtubule assembly in a cell, decrease a probability of branching in the cell, and decrease a binding between snapin and cypin.

Other substances, such as unbound cypin (or at least the portion thereof), unbound snapin (or at least the portion thereof), unbound tubulin (or at least the portion thereof), or a complex of cypin (or at least the portion thereof) and tubulin (or at least the portion thereof) can also be used to make predictions and select the test compounds based on the test compound's ability to regulate snapin-cypin complex formation, a quantity of primary processes in a cell, probability of branching, and microtubule assembly. It is within the expertise of a person of ordinary skill in the art to select the at least one parameter for evaluating the test compound's ability to regulate snapin-cypin complex formation, a quantity of primary processes in a cell, probability of branching, and microtubule assembly.

In yet another embodiment, the invention provides a screening method comprising providing a sample comprising at least a portion of snapin, adding a test compound to at least a first portion of the sample, and determining an amount of at least the portion of snapin which is phosphorylated. The magnitude of a difference between the amount of at least the portion of snapin which is phosphorylated in at least the first portion of the sample and the amount of at least the portion of snapin which is phosphorylated in at least the second portion of the sample, which does not contain the test compound, is an indication of, inter alia, the test compound's ability to alter a binding between snapin and cypin, a number of primary processes in a cell, a probability of branching in a cell or a microtubule assembly in a cell or cell-free system.

Prognosis, Diagnosis, and Monitoring of Diseases

The present invention provides methods for diagnosing cognitive disorders by detecting decreased levels of snapin. Diagnostic methods involve detecting altered levels of snapin by determining a test amount (or a normal range) of snapin gene product (e.g., mRNA, cDNA, or polypeptide, including fragments thereof) in a biological sample from a subject (human or nonhuman mammal), and comparing the test amount with the normal amount or range (i.e., an amount or range from an individual(s) known not to suffer from a cognitive disorder) for the snapin gene product. While a particular diagnostic method may not provide a definitive diagnosis of a cognitive disorder, it suffices if the method provides a positive indication that aids in diagnosis.

The present invention also provides methods for prognosing a cognitive disorder by detecting levels of snapin. Prognostic methods involve determining the test amount of a snapin gene product in a biological sample from a subject, and comparing the test amount to a prognostic amount or range (i.e., an amount or range from individuals with varying severities of a cognitive disorder) for the snapin gene product. Various amounts of the snapin gene product in a test sample are consistent with certain prognoses for cognitive disorders. The detection of an amount of snapin gene product at a particular prognostic level provides a prognosis for the subject.

The present invention also provides methods for monitoring the course of a cognitive disorder by detecting levels of snapin. Monitoring methods involve determining the test amounts of a snapin gene product in biological samples taken from a subject at a first and second time, and comparing the amounts. A change in amount of snapin gene product between the first and second time indicates a change in the course of a cognitive disorder. More specifically, if the normal range of the snapin gene product amount is closer to the snapin gene product measured at the second time than to the amount of the snapin gene product measured at the first time, the disorder has improved. Conversely, if the normal range of the snapin gene product amount is closer to the snapin gene product measured at the first time than to the amount of the snapin gene product measured at the second time, the disorder has progressed. Such monitoring assays are also useful for evaluating the efficacy of a particular therapeutic intervention (e.g., disease attenuation vs. reversal) in patients being treated for a cognitive disorder.

Biological Sample Collection

Expression of snapin can be detected in a variety of biological samples, including cells (e.g., whole cells, cell fractions, and cell extracts) and tissues. Biological samples also include sections of tissue such as biopsies and frozen sections taken for histological purposes. Preferred biological samples include blood samples, nasal biopsies, brain tissue, and spinal fluid.

Normal, Diagnostic, and Prognostic Values

In the diagnostic and prognostic assays of the present invention, the snapin gene product is detected and quantified to yield a test amount. The test amount is then compared to a normal amount or range. The test amount outside of the normal amount or range (e.g., the test amount which is significantly different (i.e., $p<0.05$)) is a positive sign in the diagnosis of a cognitive disorder. Particular methods of detection and quantification of snapin gene products are described below.

Normal amounts or baseline levels of snapin gene products can be determined for any particular sample type and population. Generally, baseline (normal) levels of snapin protein or mRNA are determined by measuring the amount of snapin protein or mRNA in a biological sample type from normal (i.e., healthy) subjects. Alternatively, normal values of snapin gene product can be determined by measuring the amount in healthy cells or tissues taken from the same subject from which the diseased (or possibly diseased) test cells or tissues were taken. The amount of snapin gene product (either the normal amount or the test amount) can be determined or expressed on a per cell, per total protein, or per volume basis. To determine the cell amount of a sample, one can measure the level of a constitutively expressed gene product or other gene product expressed at known levels in cells of the type from which the biological sample was taken.

It will be appreciated that the assay methods of the present invention do not necessarily require measurement of absolute values of snapin gene product because relative values are sufficient for many applications of these methods. It will also be appreciated that in addition to the quantity or abundance of snapin gene products, variant or abnormal snapin gene products or their expression patterns (e.g., mutated transcripts, truncated polypeptides) may be identified by comparison to normal gene products and expression patterns.

Assays for Snapin Gene Products

The diagnostic, prognostic, and monitoring assays of the present invention involve detecting and quantifying snapin gene products in biological samples. Snapin gene products include, for example, snapin mRNA and snapin polypeptide (or fragments thereof), and both can be measured using methods well known to those skilled in the art.

For example, snapin mRNA can be directly detected and quantified using hybridization-based assays, such as Northern hybridization, in situ hybridization, dot and slot blots, and oligonucleotide arrays. Hybridization-based assays refer to assays in which a probe nucleic acid is hybridized to a target nucleic acid. In some formats, the target, the probe, or both are immobilized. The immobilized nucleic acid may be DNA, RNA, or another oligonucleotide or polynucleotide, and may comprise naturally or nonnaturally occurring nucleotides, nucleotide analogs, or backbones. Methods of selecting nucleic acid probe sequences for use in the present invention are based on the nucleic acid sequence of snapin and are well known in the art.

Alternatively, snapin mRNA can be amplified before detection and quantitation. Such amplification-based assays are well known in the art and include polymerase chain reaction (PCR), reverse-transcription-PCR (RT-PCR), PCR-enzyme-linked immunosorbent assay (PCR-ELISA), and ligase chain reaction (LCR). Primers and probes for producing and detecting amplified snapin gene products (e.g., mRNA or cDNA) may be readily designed and produced without undue experimentation by those of skill in the art based on the nucleic acid sequence of snapin. Amplified snapin gene products may be directly analyzed, e.g., by gel electrophoresis; by hybridization to a probe nucleic acid; by sequencing; by detection of a fluorescent, phosphorescent, or radioactive signal; or by any of a variety of well-known methods. In addition, methods are known to those of skill in the art for increasing the signal produced by amplification of target nucleic acid sequences. One of skill in the art will recognize that whichever amplification method is used, a variety of quantitative methods known in the art (e.g., quantitative PCR) may be used if quantitation of snapin gene products is desired.

Snapin polypeptides (or fragments thereof) can be detected and quantified using various well-known enzymatic and immunological assays. Enzymatic assays refer to assays that utilize snapin substrates to detect guanine deaminase activity. Guanine deaminase activity can assayed by following the conversion of guanine to xanthine as described in, e.g., Yuan et al., *J. Biol. Chem.* 274:8175 (1999) and Paletzki, *Neuroscience* 109:15 (2002). Immunological assays refer to assays that utilize an antibody (e.g., polyclonal, monoclonal, chimeric, humanized, scFv, and fragments thereof) that specifically binds to a snapin polypeptide (or a fragment thereof). A number of well-established immunological assays suitable for the practice of the present invention are known, and include enzyme linked immunosorbent assay (ELISA), radioimmunoassay (RIA), immunoprecipitation, immunocytostaining, immunodiffusion, and Western blotting.

In the immunological assays of the present invention, the snapin polypeptide is typically detected directly (i.e., the anti-snapin antibody is labeled) or indirectly (i.e., a secondary antibody that recognizes the anti-snapin antibody is labeled) using a detectable label. The particular label or detectable group used in the assay is usually not critical, as long as it does not significantly interfere with the specific binding of the antibodies used in the assay.

The immunological assays of the present invention may be competitive or noncompetitive. In competitive assays, the amount of snapin in a sample is measured indirectly by measuring the amount of added (exogenous) snapin displaced from a capture agent (i.e., an anti-snapin antibody) by the snapin in the sample. In noncompetitive assays, the amount of snapin in a sample is directly measured. In a preferred noncompetitive "sandwich" assay, the capture agent (e.g., a first anti-snapin antibody) is bound directly to a solid support (e.g., membrane, microtiter plate, test tube, dipstick, glass or plastic bead) where it is immobilized. The immobilized agent then captures any snapin polypeptide present in the sample. The immobilized snapin can then be detected using a second labeled anti-snapin antibody. Alternatively, the second anti-snapin antibody can be detected using a labeled secondary antibody that recognizes the second anti-snapin antibody.

In other embodiments, the methods and assays of the present invention involve detection of point mutations of the snapin gene product. The point mutations may affect binding between snapin and cypin, phosphorylation of the snapin protein, or folding of the snapin protein. A person of ordinary skill in the art will appreciate that the point mutations of the snapin gene product may be determined by several methods, including, without limitation, sequencing of snapin genomic DNA, snapin cDNA (which can be obtained by, for example, RT-PCR) or snapin protein.

As discussed both above and below, serine at position 50 of the snapin amino acid sequence can be phosphorylated. Mutations of serine at position 50 alter the rate of formation of the complex between the snapin protein and the cypin protein. A mutation comprising S50A mimics the unphosphorylated form of the snapin protein while a mutation comprising S50D mimics the phosphorylated form of the snapin protein. The inventors have found that only the unphosphorylated form binds to cypin, thus suggesting that phosphorylation of snapin negatively regulates its association with cypin. Accordingly, in yet other embodiments, the assays and methods of the present invention involve determination of phosphorylation of the snapin protein. It is within the expertise of a person of ordinary skill in the art to select a phosphorylation assay to measure a phosphorylation rate of snapin. A non-limiting example of such assay is an immunological assay with an antibody specifically recognizing either a phosphorylated form or an unphosphorylated form of snapin only.

As described below, the inventors found that snapin competes with tubulin for cypin. Accordingly, quantitative characteristics of this competition may be used to determine effects of a test compound on a microtubule formation, a number of primary processes in the cell, and a probability of branching.

Thus, in one embodiment, provided is a screening method comprising providing a sample containing at least a portion of cypin and at least a portion of snapin; adding a test compound to at least a first portion of the sample; and determining at least one parameter selected from the group consisting of: a) an amount of a complex between at least the portion of cypin and at least the portion of snapin, b) an amount of at least the portion of snapin not bound to at least the portion of cypin, c)

an amount of at least the portion of cypin not bound to at least the portion of snapin, and any combination thereof.

In another embodiment, the method comprises providing a sample containing at least a portion of cypin and at least a portion of snapin; adding at least the portion of tubulin to the sample; adding a test compound to at least a first portion of the sample; and determining at least one parameter selected from the group consisting of: a) an amount of a complex between at least the portion of cypin and at least the portion of snapin, b) an amount of at least the portion of snapin not bound to at least the portion of cypin, c) an amount of at least the portion of cypin not bound to at least the portion of snapin, d) an amount of a complex between at least the portion of cypin and at least the portion of tubulin, e) an amount of at least the portion of tubulin not bound to at least the portion of cypin, and any combination thereof.

The screening assays used to quantify the at least one parameter can be either cell-based or cell-free assays. Cell-free assays are preferred because they are easily adaptable to high-throughput screening procedures (e.g., BIACORE™ (Biacore International AB, Uppsala, Sweden), BRET (bioluminescence resonance energy transfer), FRET (fluorescence resonance energy transfer), ELISA, spectrophotometric tubulin binding and tubulin polymerization assays, etc.

Upon comparing the at least one parameter from at least the first portion of the sample with the at least one parameter from either at least a second portion of the sample, which does not include the test compound, or with pre-set standards (i.e. pre-calibrated standard curve), a user of any of the method described above may make predictions about and select the appropriate test compound based on the test compound's ability to alter a binding between snapin and cypin, to alter a number of primary processes in a cell, to alter a probability of branching in a cell, and/or to alter a microtubule assembly in a cell.

For example, an increase in the amount of at least the portion of cypin bound to at least the portion of snapin indicates an ability of the test compound to inhibit a microtubule assembly in a cell, decrease a number of primary processes in the cell, increase a probability of branching in the cell, and increase a binding between snapin and cypin. A decrease in the amount of at least the portion of cypin bound to at least the portion of snapin indicates an ability of the test compound to decrease a quantity of primary processes in a cell, induce a microtubule assembly in a cell, decrease a probability of branching in the cell, and decrease a binding between snapin and cypin.

The at least one parameter based on other compounds can also be used to make predictions and select the test compounds based on the test compound's ability to regulate snapin-cypin complex formation, a quantity of primary processes in a cell, probability of branching, and microtubule assembly. It is within the expertise of a person of ordinary skill in the art to select the at least one parameter for evaluating the test compound.

The at least one parameter can be readily determined by any number of assays widely known in the art, such as for example, a competition or sandwich ELISA, a radioimmunoassay, a dot blot assay, a fluorescence polarization assay, a scintillation proximity assay, a homogeneous time resolved fluorescence assay, a resonant mirror biosensor analysis, and a surface plasmon resonance analysis.

In different embodiments of the invention, at least one compound selected from the group consisting of the test compound, at least the portion of tubulin, at least the portion of snapin and at least the portion of cypin, can be labeled with a marker. Suitable markers are widely known in the art and include various enzymes, prosthetic groups, fluorescent materials, luminescent materials, magnetic agents and radioactive materials. Non-limiting examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; examples of a luminescent material include luminol luciferin, pyrogallol, or isoluminol; an example of a magnetic agent includes gadolinium; and examples of suitable radioactive material include $^{125}$I, $^{131}$I, $^{35}$S or $^{3}$H.

Methods, kits, equipment, and instructions for these methods are available from multiple manufacturers including, without limitation, Pierce Chemical Co. (Rockford, Ill.), IMx®, TDx®, and TDxFLx™. (Abbott Laboratories, Abbott Park, Ill.), Amersham Life Science (Piscataway, N.J.), and BIACORE® (Biacore A B, Uppsala, Sweden).

Possible modifications of these assays will be apparent to a person of ordinary skill in the art. The claims of the present invention include all such modifications.

Another aspect of invention provides multiple kits. In one embodiment, the invention provides a kit comprising least the portion of cypin, at least the portion of cypin being capable of binding tubulin; and at least the portion of snapin, at least the portion of snapin being capable of binding at least the portion of cypin.

In another embodiment, the kit further comprises at least a portion of tubulin, said portion of tubulin capable of binding at least the portion of cypin. As described above, at least the portions of snapin and cypin include amino acid sequences capable of binding to each other (i.e. the CRMP domain of cypin and the coiled coil domain of snapin). In other embodiments, at least the portions of cypin and snapin comprise sequences responsible for regulation of binding between these sequences.

In another embodiment, at least one substance selected from the group consisting of at least the portion of cypin, at least the portion of snapin, and at least the portion of tubulin, is immobilized. The immobilization can be achieved by attaching the at least one substance to a column, such as, for example, an affinity chromatography column, or to a well of, for example, a testing plate. Furthermore, the at least one substance can be labeled with a marker, such as, for example, one of the markers described above.

In another embodiment, the kit further comprises a set of instructions for efficient and safe use of the kit. A person skilled in the art will undoubtedly appreciate that the set of instruction may be provided in any medium, including, without limitations, printed, audio and video recorded, and electronic.

In yet another embodiment, a kit comprises a set of primers capable of selectively binding to different portions of snapin mRNA or snapin cDNA supporting a replication of at least the portion of snapin mRNA or snapin cDNA. In addition, the kit may optionally comprise at least one at least one substance selected from the group consisting of a polymerase enzyme (such as, for example, reverse transcriptase), a marker (such as, for example, Cy-3 or Cy-5), a set of dNTPs, and a set of instructions.

In another aspect, this invention provides methods for prognosing, diagnosing, treating, and monitoring cognitive diseases. In one embodiment, the method for use in the diagnosis of a cognitive disorder in a subject comprises detecting a test amount of a snapin gene product in a sample from the subject; and comparing the test amount with a normal amount of snapin gene product in a control sample, whereby a finding that the test amount is outside of the normal range for the snapin gene product provides a positive indication in the diagnosis of a cognitive disorder.

In another embodiment, the method comprises detecting a test amount of a phosphorylated snapin protein in a sample from the subject and comparing the test amount with a normal amount of the phosphorylated snapin protein in a control sample, whereby the amount in the test sample outside of the control range provides a positive indication in the diagnosis of a cognitive disorder.

The method for use in the prognosis of a cognitive disorder in a subject comprises the steps of: detecting a test amount of a snapin gene product in a sample from the subject; and comparing the test amount with prognostic amounts of the snapin gene product in control samples, whereby a comparison of the test amount with the prognostic amounts provides an indication of the prognosis of cognitive disorder.

In another embodiment, the method comprises detecting a test amount of a phosphorylated snapin protein in a sample from the subject and comparing the test amount with a normal amount of the phosphorylated snapin protein in a control sample, whereby a comparison of the test amount with the normal amounts provides an indication of the prognosis of cognitive disorder.

The method for use in monitoring the course of a cognitive disorder in a subject comprises the steps of: detecting a first test amount of a snapin gene product in a sample from the subject at a first time; detecting a second test amount of the snapin gene product in a sample from the subject at a second, later time; and comparing the first test amount and the second test amount, whereby the normal range of the snapin gene product amount closer to the snapin gene product measured at the second time than to the amount of the snapin gene product measured at the first time indicates that the disorder has improved; and the normal range of the snapin gene product amount closer to the snapin gene product measured at the first time than to the amount of the snapin gene product measured at the second time indicates that the disorder has progressed.

In another embodiment, the method comprises the steps of: detecting a first test amount of a phosphorylated snapin protein in a sample from the subject at a first time; detecting a second test amount of the phosphorylated snapin protein in a sample from the subject at a second, later time; and comparing the first test amount and the second test amount, whereby the normal range of the phosphorylated snapin protein amount closer to the phosphorylated snapin protein measured at the second time than to the amount of the phosphorylated snapin protein measured at the first time indicates that the disorder has improved; and the normal range of the phosphorylated snapin protein amount closer to the phosphorylated snapin protein measured at the first time than to the amount of the phosphorylated snapin protein measured at the second time indicates that the disorder has progressed.

The method for assessing the efficacy of a treatment for a cognitive disorder in a subject comprises the steps of: detecting a first test amount of a snapin gene product in a sample from the subject prior to treatment; detecting a second test amount of the snapin gene product in a sample from the subject after treatment; and comparing the first test amount and the second test amount, whereby the normal range of the snapin gene product amount closer to the snapin gene product measured at the second time than to the amount of the snapin gene product measured at the first time indicates that the treatment is efficient; and the normal range of the snapin gene product amount closer to the snapin gene product measured at the first time than to the amount of the snapin gene product measured at the second time indicates that the treatment is not efficient.

In another embodiment, the method comprises the steps of: detecting a first test amount of a phosphorylated snapin protein in a sample from the subject at a first time; detecting a second test amount of the phosphorylated snapin protein in a sample from the subject at a second, later time; and comparing the first test amount and the second test amount, whereby the normal range of the phosphorylated snapin protein amount closer to the phosphorylated snapin protein measured at the second time than to the amount of the phosphorylated snapin protein measured at the first time indicates that the treatment is efficient; and the normal range of the phosphorylated snapin protein amount closer to the phosphorylated snapin protein measured at the first time than to the amount of the phosphorylated snapin protein measured at the second time indicates that the treatment is not efficient.

The methods for prognosing, diagnosing, treating, and monitoring the at least one cognitive diseases may be practicing the kits of the present invention disclosed above.

Specific embodiments according to the methods of the present invention will now be described in the following non-limiting examples.

EXAMPLES

Example 1

Cypin and Snapin Interact In Vitro

Affinity Chromatography.

COS-7 cells were transfected with either pEGFP-C1-snapin, pDsRed-N1-snapin, pEGFP-C1-cypin or pDsRed-N1-cypin using Lipofectamine 2000 (Invitrogen, Carlsbad, Calif.) as described by manufacturer. Cells were washed with cold PBSE (phosphate buffered saline and 1 mM EDTA) and scraped into 5 mL of TEEN (25 mM Tris-HCl, pH 7.4, 1 mM EDTA, 1 mM EGTA, 100 mM NaCl). Cells were homogenized using a Potter-Elvehjem tissue grinder (20 strokes). Phenylmethylsulfonyl fluoride and DTT were added to lysates to final concentrations of 1 mM and cells were further lysed by passing the extract through a 25 gauge needle 5 times. Lysates were centrifuged at 12,000×g for 10 minutes at 4° C. Triton X-100 was added to the supernatant to a final concentration of 1% and incubated at 4° C. for 30 minutes. Lysates were centrifuged at 12,000×g for 10 minutes at 4° C. COS-7 cell lysates were incubated with glutathione-sepharose beads bound to 25 μg of the appropriate GST-fusion proteins for 1 hour at 4° C. Beads were washed three times with TEEN. Bound proteins were eluted with 0.5% SDS and 100 mM NaCl. Proteins were resolved on a 10% SDS polyacrylamide gel and transferred to PVDF membrane. Blots were probed with the indicated antibodies. For experiments using rat brain extracts, the extracts were prepared exactly as described above except that they were not passed through a 25 gauge needle. Experiments were performed in duplicate or triplicate.

Co-Immunoprecipitation.

For co-immunoprecipitation studies, one rat brain was homogenized in 10 ml of TEE (25 mM Tris, 1 mM EGTA, 1 mM EDTA)+1 mM PMSF. Triton X-100 was added to a final concentration of 1% and proteins were extracted for 1 hour at 4° C. The extract was centrifuged at 12,000×g to remove insoluble material and the supernatant was incubated with either anti-cypin, anti-snapin, preimmune serum, rabbit IgG, anti-tubulin, or mouse IgG. Protein A beads were added and after a 1 hour incubation, the beads were washed with TEE+ 0.2% Triton X-100. Immunoprecipitated proteins were eluted with protein loading buffer and resolved by SDS-PAGE and transferred to PVDF membrane. Blots were probed with the indicated antibodies. Experiments were performed in duplicate or triplicate.

For quantitation of co-immunoprecipitates, immunoreactive bands were selected from scanned blots and intensities were quantitated using Adobe Photoshop® software. An area close to the bands was used as a reference for background intensity. Number of pixels for the precipitate bands was compared to that of the input (load) to give percentage precipitated. This percentage was then adjusted for amount of input relative to the amount of eluate run for analysis.

To identify where snapin binds on cypin, we performed affinity chromatography using maltose binding protein fusions of cypin regions and extracts of COS-7 cells expressing GFP-snapin. As shown in FIG. 1A, snapin binds to the C-terminal half of cypin, as evidenced by lack of binding to amino acids 1-120, 1-220, and 1-350 and positive binding to amino acids 221-end and 350-end of cypin. Snapin binds to the region of cypin containing the collapsin response mediator protein (CRMP) homology domain (amino acids 350-403, FIG. 1B), as evidenced by binding to amino acids 350-end. Snapin binding was disrupted when the CRMP homology domain was deleted (cypinΔ350-403; FIG. 1B). These data thus suggest that cypin's CRMP homology domain serves as the snapin binding site.

To identify the region of snapin that binds to cypin, GST-affinity chromatography using either the entire 136 amino acids or the first 68 amino acids of snapin on the column and rat brain extract was performed. As shown in FIGS. 1C and 1D, full-length but not the first half of snapin binds to cypin. Previously, two groups reported the presence of a carboxyl-terminal coiled-coil domain in the second half of snapin (Ilardi et al., 1999; Ruder et al., 2005). This domain was defined as slightly different regions by both groups. To determine which region binds to cypin, GST-afffinity chromatography with amino acids 81-126 and 83-119 was performed. Surprisingly, only 81-126 bound, suggesting that this is the minimal domain necessary for snapin's binding to cypin. Thus, the carboxyl-terminal coiled-coil domain of snapin is required for interaction with the CRMP homology domain of cypin.

Example 2

Snapin and Cypin Interact In Vivo

To demonstrate that snapin and cypin could interact in brain co-immunoprecipitation studies using brain extracts were performed.

Co-Immunoprecipitation.

For co-immunoprecipitation studies, one rat brain was homogenized in 10 ml of TEE (25 mM Tris, 1 mM EGTA, 1 mM EDTA)+1 mM PMSF. Triton X-100 was added to a final concentration of 1% and proteins were extracted for 1 hour at 4° C. The extract was centrifuged at 12,000×g to remove insoluble material and the supernatant was incubated with either anti-cypin, anti-snapin, preimmune serum, rabbit IgG, anti-tubulin, or mouse IgG. Protein A beads were added and after a 1 hour incubation, the beads were washed with TEE+ 0.2% Triton X-100. Immunoprecipitated proteins were eluted with protein loading buffer and resolved by SDS-PAGE and transferred to PVDF membrane. Blots were probed with the indicated antibodies. Experiments were performed in duplicate or triplicate.

For quantitation of co-immunoprecipitates, immunoreactive bands were selected from scanned blots and intensities were quantitated using Adobe Photoshop® software. An area close to the bands was used as a reference for background intensity. Number of pixels for the precipitate bands was compared to that of the input (load) to give percentage precipitated. This percentage was then adjusted for amount of input relative to the amount of eluate run for analysis.

Figure 2:
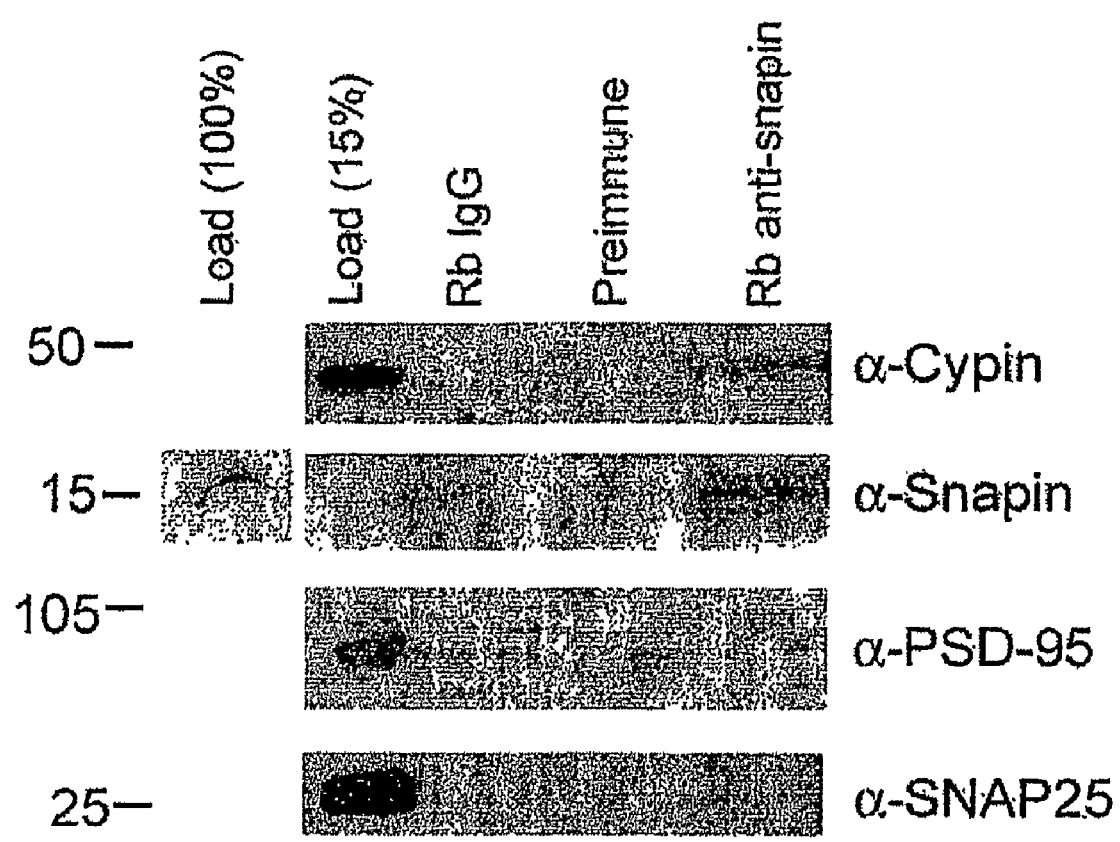
FIG. 2 illustrates the results of experiments demonstrating that snapin and cypin interact in vivo.

As shown in FIG. 2, approximately 10% of cypin co-immunoprecipitates when all of snapin is precipitated. Furthermore neither PSD-95 nor SNAP-25 is detected in these immunoprecipitates, showing that the interaction between cypin and snapin is specific. In parallel, approximately 20% of snapin co-immunoprecipitates with cypin. Snapin is not co-immunoprecipitated with tubulin or mouse or rabbit IgG. In addition, a doublet is seen in the cypin immunoprecipitate. The smaller protein may be a degradation product or a post-translationally modified snapin. As expected, cypin is precipitated when antisera to cypin was used, and tubulin is precipitated when antisera to tubulin is used. Thus, these data suggest that snapin and cypin exist in a complex in the brain.

Example 3

Snapin is Present in the Cell Body and Dendrites of Developing Neurons

Neuronal Culture, Immunohistochemistry, and Transfection.

Neuronal cultures were prepared from hippocampi of rat embryos at 18 days gestation. The hippocampi were dissociated by brief mechanical trituration. Cells were plated on poly-D-lysine coated glass coverslips (12 mm in diameter) at a density of approximately 1800 cells/mm$^2$. Cultures were plated and maintained in Neurobasal media supplemented with B27, penicillin, streptomycin, and L-glutamine. For immunocytochemistry, neurons were fixed in 4% paraformaldehyde in phosphate-buffered saline for 15 minutes and labeled with the appropriate antibody. Labeled cells were visualized by immunofluorescence (Olympus IX50 microscope with a Cooke Sensicam CCD cooled camera, fluorescence, imaging system and Image Pro software). For transfection, neurons were grown for 10 days in culture and transfected with the appropriate constructs using Effectene (Qiagen). Neurons were allowed to express the transfected protein for 48 hours and then used for assay of dendrite number.

For immunostaining, neurons were fixed in 4% paraformaldehyde in phosphate buffered saline (PBS) for 15 minutes. Cells were then incubated in blocking solution (PBS containing 0.1% Triton X, 2% normal goat serum and 0.02% sodium azide) for 1 hour. All antibodies used were diluted in blocking solution. For snapin and TGN staining, 1:500 dilutions of primary antibodies were used. For snapin and synaptophysin staining, 1:250 dilutions of primary antibodies were used. For snapin and early endosome staining, 1:250 dilutions of primary antibodies were used. For snapin-GFP and cypin staining, dilutions of 1:100 for rabbit anti-cypin and 1:1000 for rat anti-GFP were used. All incubations with primary antibodies were performed at room temperature on an orbital shaker for two hours. Coverslips were then washed with PBS three times. Secondary antibody consisted of a 1:250 dilution of Cy2 conjugated donkey anti-rabbit IgG and Cy3 conjugated donkey anti-mouse IgG. For snapin-GFP and cypin immunostaining, the secondary antibodies were a 1:250 dilution of Cy2 conjugated donkey anti-rat IgG and Cy3 conjugated donkey anti-rabbit IgG. All labeling with secondary antibodies was performed at room temperature on an orbital shaker for one hour. Washes were performed as stated above. Coverslips were then mounted onto frosted glass microscope slides using Fluormount G.

To assess where snapin is localized in developing neurons in order to identify what role snapin may play by binding to cypin, immunocytochemistry using cultures of hippocampal neurons at 7 d.i.v. and 12 d.i.v. was performed. The time points were selected since cypin plays a role in primary and secondary dendrite development at this time (Akum et al., 2004). As seen in FIG. 3A, snapin is found in the cell body and in dendrites. This localization is seen at both time points and is similar to cypin localization. Since both antibodies used for immunostaining were raised in rabbits, it was not possible to perform double-staining to compare the endogenous expression patterns of snapin and cypin in a single neuron. As an alternative, hippocampal neurons were transfected with a cDNA encoding GFP-snapin, immunostained for endogenous cypin, and performed confocal imaging.

Snapin and cypin proteins are both present outside of the nucleus, where they may co-localize (data not shown). In addition, there does not appear to be an enrichment of co-localization at any specific organelle (data not shown). Thus, these data suggest that snapin and cypin have similar expression patterns in developing hippocampal neurons.

Developmental Western Blot

Hippocampal neurons were plated at 1 million cells per 35 mm dishes. At 10, 12, 17, and 24 d.i.v., cells were washed with ice cold 1×PBS and scraped into TEE containing 150 mM NaCl and 1 mM PMSF. Cells were homogenized using a Potter-Elvehjem tissue grinder (20 strokes) and further lysed by passing the extract through a 25 gauge needle 5 times. Lysates were centrifuged at 14,000×g for 10 min at 4° C. Proteins were resolved on a 15% SDS polyacrylamide gel and transferred to PVDF membrane. The blot was probed with the indicated antibodies.

Snapin protein is expressed at very low levels at 2 d.i.v., when primary branching occurs. Snapin expression increases by 7 d.i.v., when primary dendrite formation is slowing down and higher order branching is occurring (FIG. 3B). Furthermore, snapin protein expression is maintained by 17 d.i.v. when spine formation is occurring. Thus, the expression pattern of snapin suggests that it may differentially regulate dendrite formation and/or branching.

Example 4

Snapin and Cypin are Expressed in a Number of Synaptosomal Fractions

Four rat cortices were homogenized in 36 ml of homogenization buffer (320 mM sucrose, 4 mM HEPES, pH 7.4, 1 mM EGTA, 1 mM PMSF) using 10 strokes at 900 rpm of a loose fitting glass-Teflon homogenizer (Kontes; size 22). The homogenate was centrifuged at 1000×g for 10 min. The supernatant (S1) was collected and centrifuged at 12,000×g for 15 min, and the pellet (P2) was resuspended in 24 ml of homogenization buffer and centrifuged at 13,000×g for 15 min. The resulting pellet (P2'), representing a crude synaptosomal fraction, was lysed by osmotic shock and homogenized by three strokes of the glass-Teflon homogenizer at 2000 rpm, and the homogenate was spun at 33,000×g for 20 min to yield supernatant (LS1) and pellet (LP1, heavy membranes). LS1 was spun at 251,000×g max for 2 h. The resulting supernatant (LS2) contained soluble proteins, and the pellet (LP2) contained synaptic vesicle proteins. Proteins were resolved on a 10% SDS-polyacrylamide gel, and Western blotting was performed as described above.

Pixel intensities of homogenate, P2 and S2 were determined by using Adobe Photoshop 5®. Luminosity of each band was determined using the histogram function. Mean luminosity and total pixels were determined for each of the three samples on each film. Background for each band was taken of an area on the film close to the band. And mean luminosity and total pixels were also determined for background. Mean luminosities were multiplied by total pixels to obtain total luminosity for each band and background. Total luminosity for each band was divided by luminosity of the corresponding background to normalize. Averages were taken for each sample (n=2) and SEM was determined.

Figure 4:
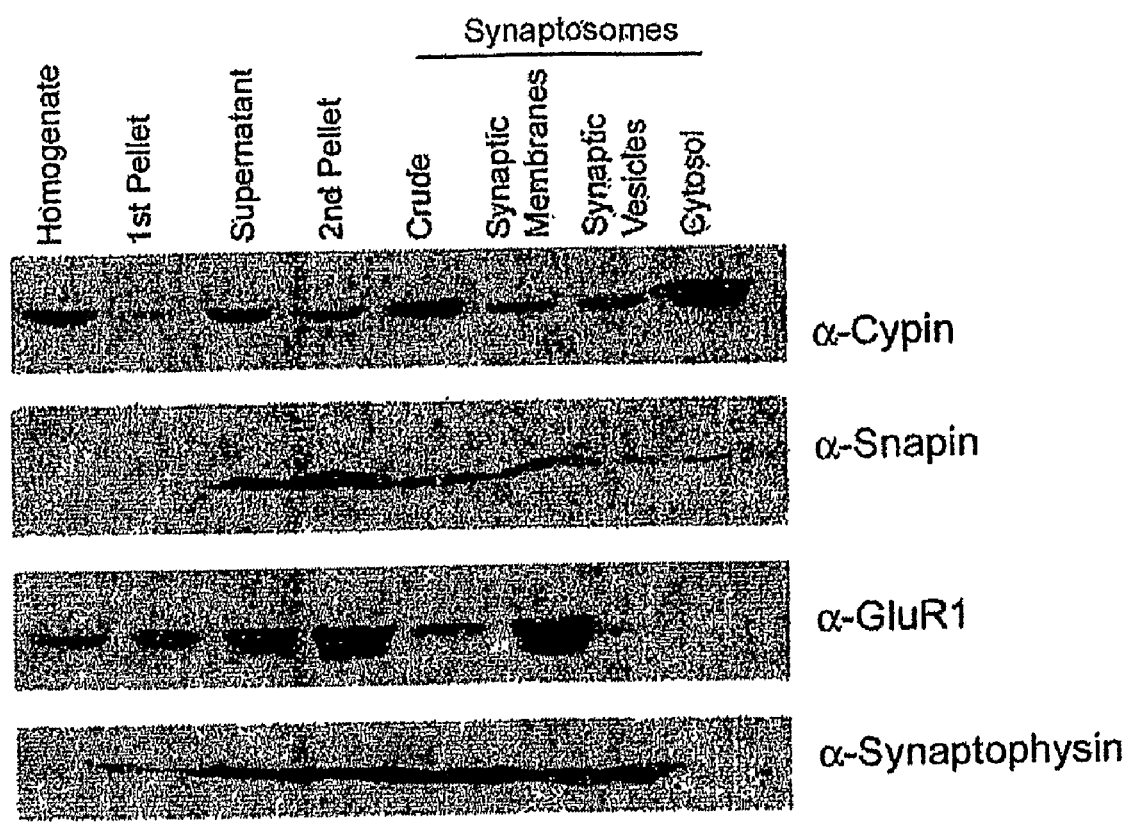
FIG. 4 illustrates the results of experiments showing that both cypin and snapin are expressed in synaptosomal fractions.

These data suggest a role for snapin in the cell body or proximal dendrites. However, it is unclear from the literature whether snapin is exclusively localized to synaptic vesicles (Ilardi et al., 1999) or not (Vites et al., 2004). To assess where snapin is localized in rat brain, Western blotting of synaptosomal fractions was performed. Snapin was found in all synaptosomal fractions (FIG. 4). Cypin is also found in all synaptosomal fractions. The efficiency of fractionation was verified with GluR1, a membrane receptor subunit that is enriched in the synaptic membrane fraction, and synaptophysin, a synaptic vesicle marker that is enriched in the synaptic vesicle fraction. Thus, snapin may play a role at sites other than synaptic vesicles and that it may regulate cypin function at various sites in the neuron.

Example 5

Snapin is Localized to Both the Membrane and Cytosol

Figure 5:
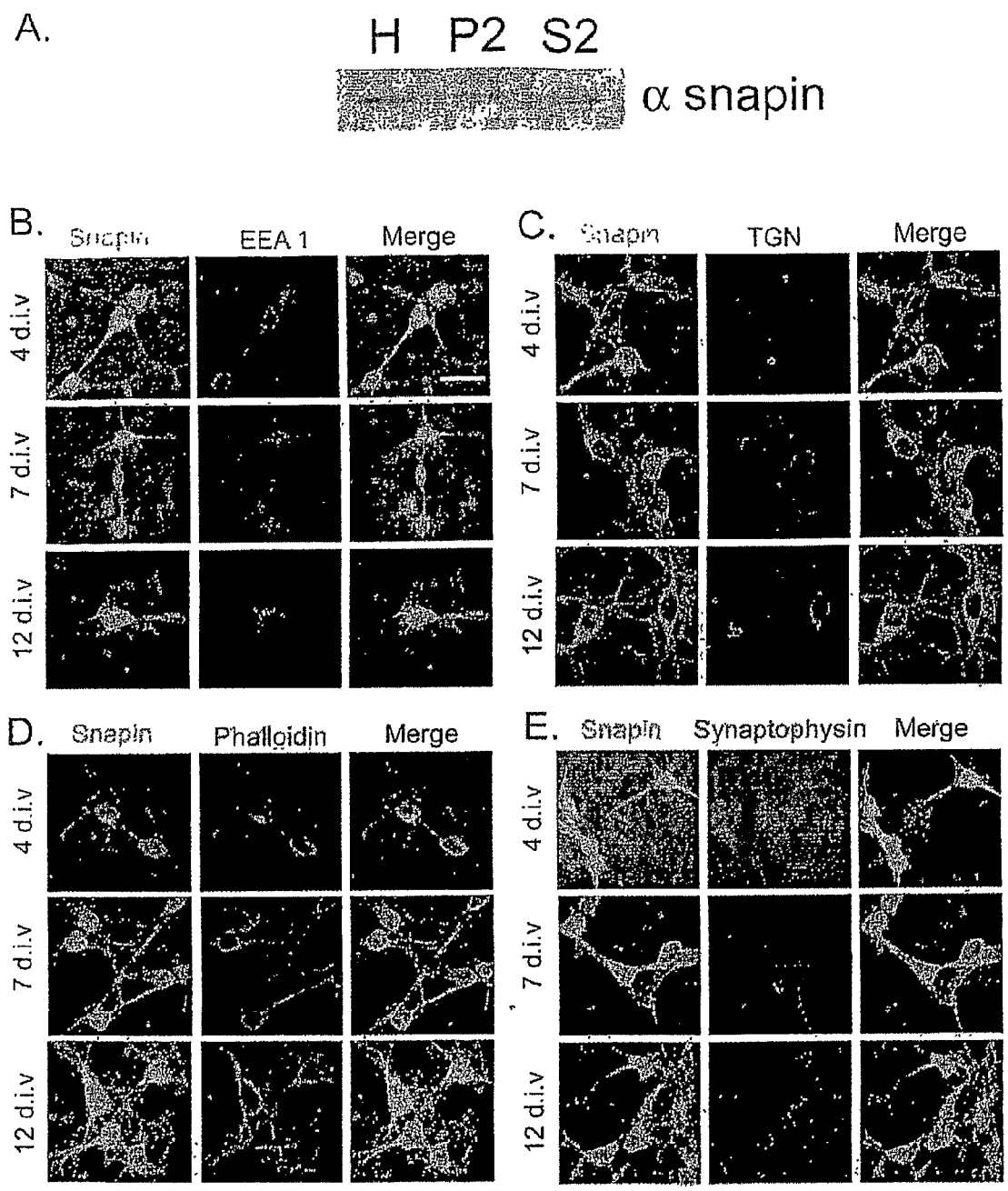
FIG. 5 shows that snapin is localized in both membrane and cytosol.

To gain additional insight into how snapin may act to regulate neuronal development, the relative amounts of snapin protein in membrane-associated (P2) and soluble (S2) fractions were analyzed. As seen in FIG. 5A, there are equal amounts of snapin in the membrane associated and soluble fractions (p>0.05 by t-test for band intensity values of 2.38±0.14 (P2) and 2.12±0.54 (S2) arbitrary units over background, n=2). To determine where in the neuron snapin is localized, we performed confocal analysis of neurons immunostained for snapin and a set of organelle markers. As seen in FIGS. 5B, 5C, and 5E, snapin does not appear to colocalize with EEA1, an endosomal marker, TGN-38, a trans-Golgi network marker, or synaptophysin, a synaptic marker. A fraction of snapin is found at the plasma membrane (FIG. 5D). Thus, snapin appears to be both membrane associated and cytosolic.

Example 6

Snapin is Enriched in the Cell Bodies of Hippocampal Neurons

Figure 3:
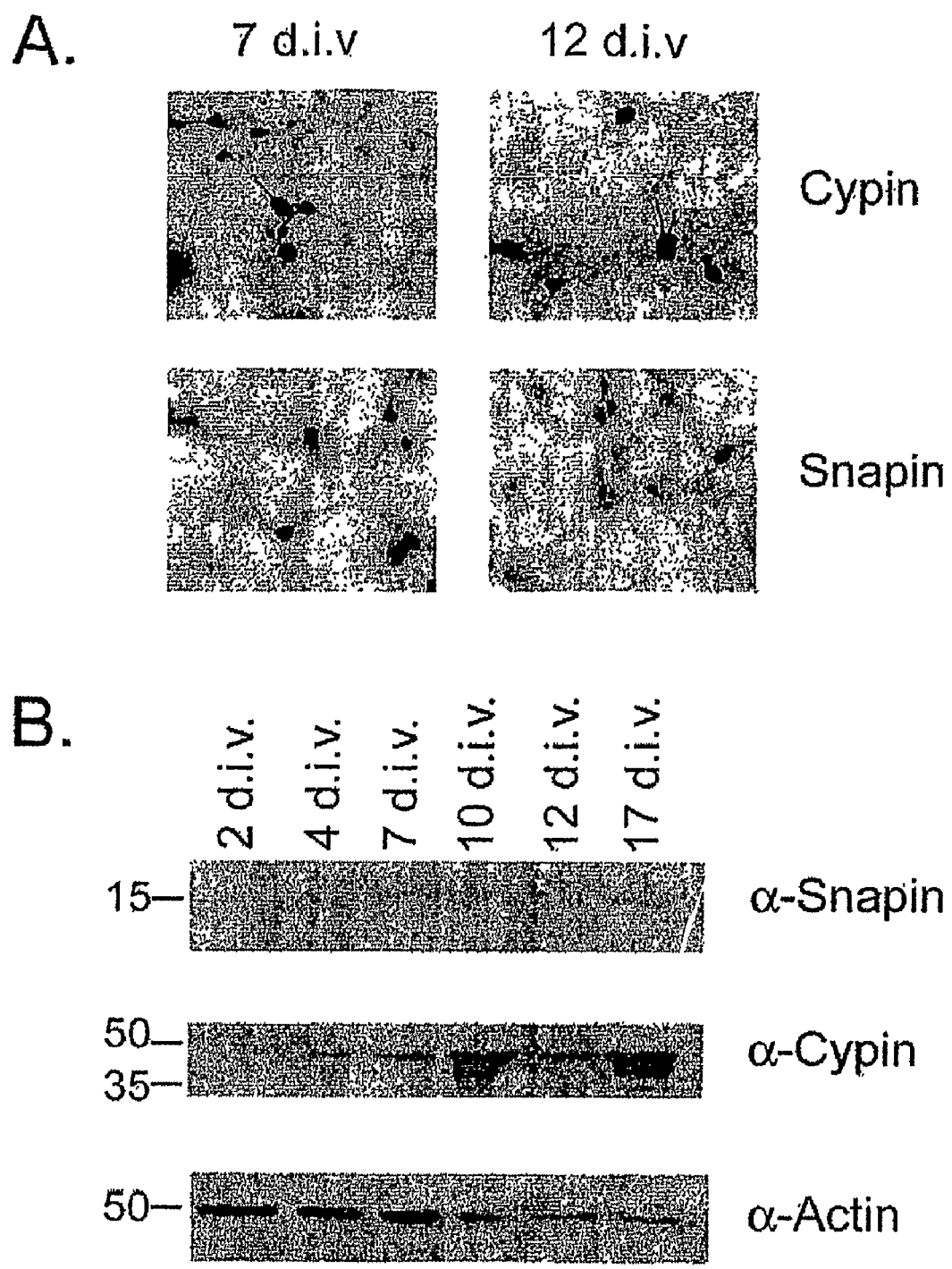
FIG. 3 shows that snapin is present in the cell body and dendrites of developing neurons.
Figure 6:
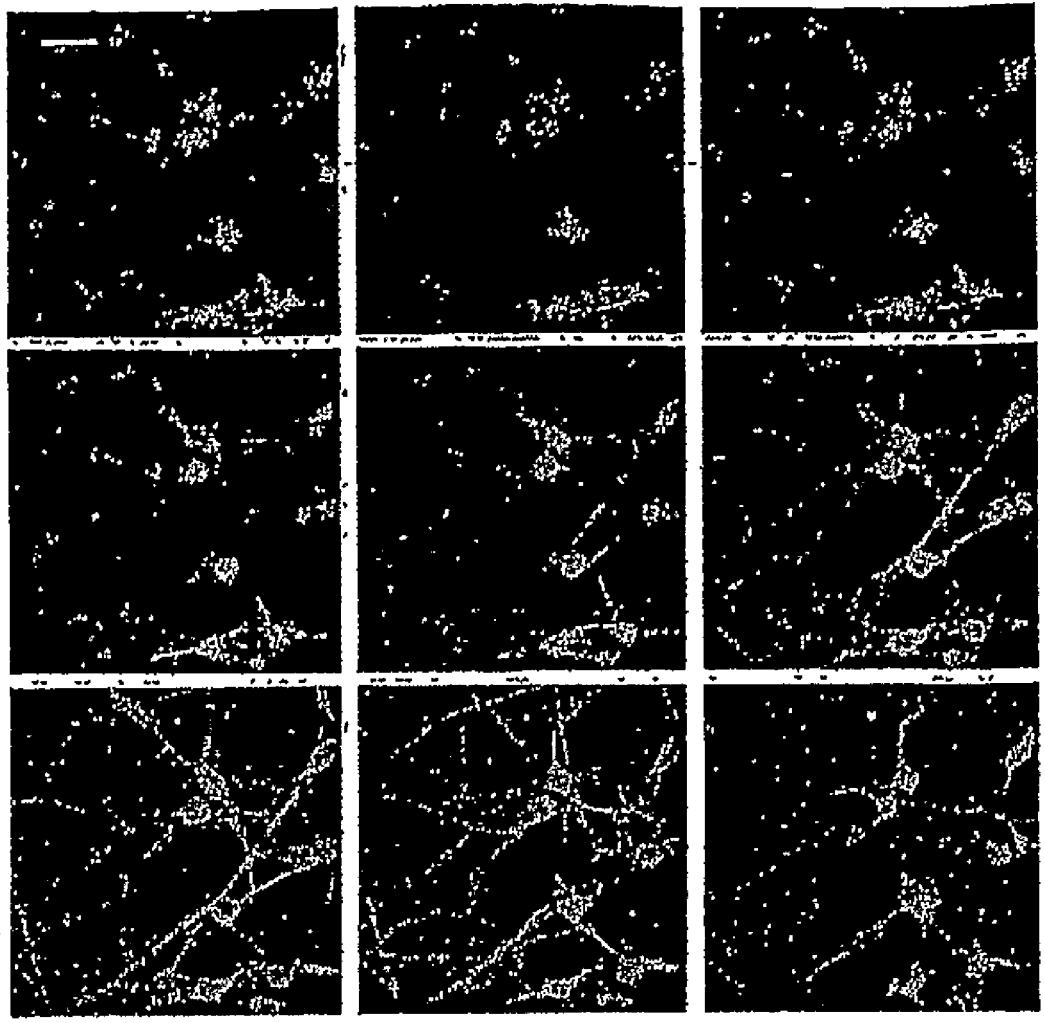
FIG. 6 shows that snapin is enriched in the cell bodies of developing hippocampal neurons.

To address how snapin could differentially affect primary and secondary dendrites, a confocal z-stack of neurons immunostained for endogenous snapin was analyzed (FIG. 6) for pixel intensities of snapin in the soma versus in the dendrites. Snapin is expressed at a higher level in the cell body than in the dendrites (22.61±0.97 versus 11.15±1.29 average brightness per pixel for 5 neurons, p<0.0001 by Student's t-test). Since cypin is expressed in both the soma and dendrite (Akum et al., 2004; FIG. 3), these data suggest that snapin and cypin may primarily interact in the cell body of developing hippocampal neurons.

Example 7

Snapin Competes Tubulin Heterodimer Binding to Cypin and Slows Cypin-Promoted Microtubule Assembly Tubulin Binding Assays.

GST, GST-cypin, and GST-snapin were expressed in *E. coli* and purified using glutathione sepharose as previously described (Firestein et al., 1999). Purified proteins were eluted from the beads using glutathione and dialyzed against phosphate buffered saline. Purified cypin (2 µM) and the indicated concentrations of purified snapin were mixed with tubulin heterodimers (7 µM) in PEM buffer (80 mM PIPES, pH 6.9, 2 mM $MgCl_2$, 0.5 mM EGTA) containing 5% glycerol for 4-6 hours at 4° C. The mixtures were subjected to immunoprecipitation using a monoclonal antibody raised against tubulin. Binding of purified proteins was assayed by SDS-PAGE followed by Western blotting using a rabbit polyclonal antibody raised against cypin (Akum et al., 2004).

Microtubule Polymerization Assays.

Tubulin (30 µM) was mixed with purified protein (2 µM) in PEM buffer containing 5% glycerol and 1 mM GTP on ice. The mixture was then incubated at 37° C., and tubulin polymerization was detected by measuring the absorbance of the solution at 340 nm over time.

Confocal Analysis.

Images were collected through a NIKON C1 laser-scanning confocal unit mounted on a Nikon TE300 inverted microscope. A Nikon 60X Plan Apo objective with numeric aperture of 1.4 was used for microscopy. The C1 confocal unit consists of two lasers (argon and HeNe) for fluorescent excitation at 488 nm and 543 nm and two individual photomultiplier tubes (PTMs) for collecting both channels of fluorescence. Scanning was performed at the resolution of 512×512 with the pinhole size set at medium and the PMT gain set at 6.0. Quantitation of snapin immunostaining was performed with Image Pro software.

For intensity studies, hippocampal neurons were stained with snapin primary antibody. Intensities for confocal z-stack images were measured using Image Pro software. Somas for each neuron were traced, and intensities were measured as average pixel intensity within the selected region. Dendrite intensities were measured by tracing dendrites and intensities were measured as average pixel intensity within selected region.

Figure 7:
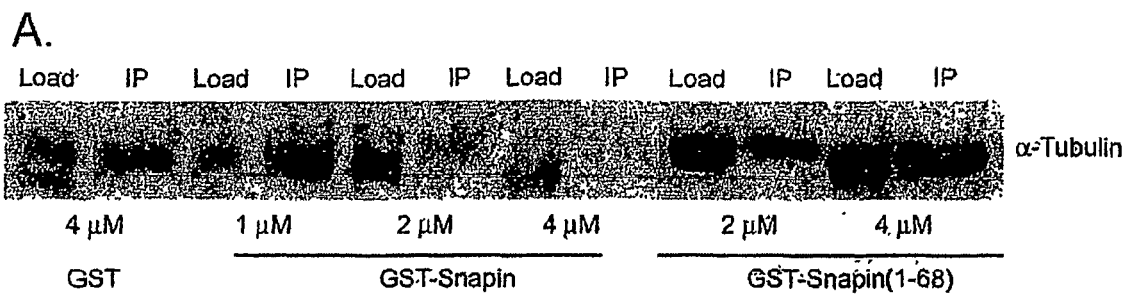
FIG. 7 shows results of experiments demonstrating that snapin competes with tubulin binding to cypin and slows cypin-promoted microtubule assembly.
Figure 7:
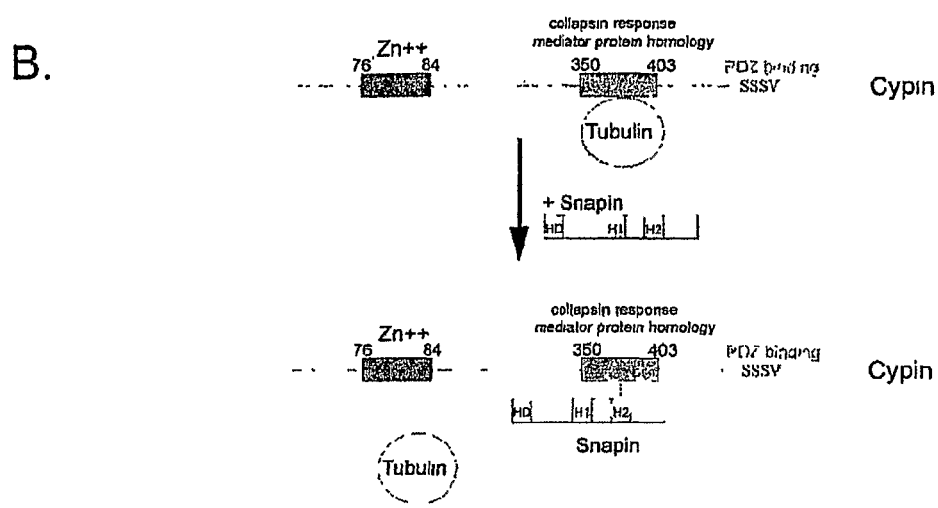
Figure 7:
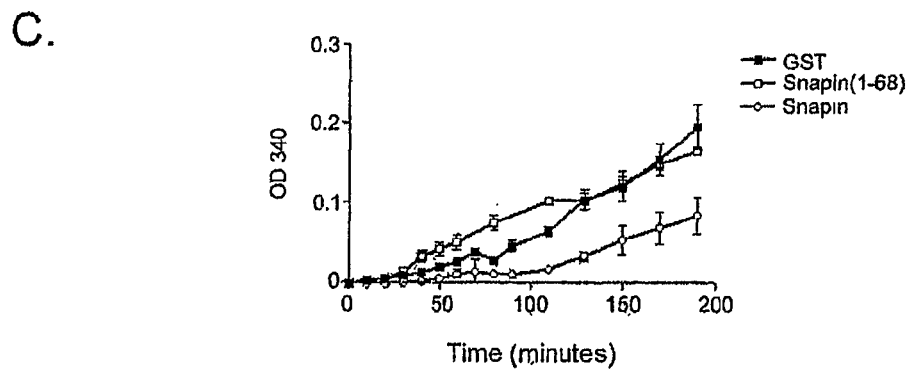

Since snapin binds to cypin's CRMP homology domain, which is responsible for binding tubulin heterodimers (Akum et al., 2004), it is possible that snapin could compete tubulin binding to cypin. To address this question, co-immunoprecipitation of purified cypin and tubulin heterodimers in the presence of full-length snapin or the N-terminal half of snapin (amino acids 1-68) was performed. No association of snapin with tubulin heterodimers by co-immunoprecipitation or affinity chromatography was found in the previous experiments (data not shown). Full-length snapin, but not the N-terminal half of snapin or GST, competes tubulin heterodimer binding to cypin (FIG. 7A). In addition, 4 µM of snapin almost fully competed tubulin heterodimer (7 µM) binding to 2 µM cypin. These data suggest a model whereby one tubulin heterodimer binds to the CRMP homology domain of cypin (Akum et al., 2004; FIG. 7B). Snapin can compete this binding, and it has higher affinity for cypin as evidenced by the fact that it takes only 4 µM snapin to compete 7 µM tubulin from cypin. Furthermore, this competition results in a slower rate of cypin-promoted microtubule assembly that is not seen in the presence of the first half of snapin or GST (FIG. 7C). Thus, the binding of snapin to cypin may act to modulate microtubule assembly by regulating tubulin heterodimer binding.

Example 8

Overexpression of Snapin Results in Changes in Dendrite Branching in Hippocampal Neurons Assessment of Dendrite Number.

Neurons were fixed and stained as above. Pictures of the transfected neurons were taken as described above. Primary and secondary dendrites were counted as previously described (Akum et al., 2004). The person analyzing the dendrite counts was blinded to the transfection condition. Dendrite counts were performed by at least two people, and a third person unblinded the data. Dendrites were counted if they were $\geq 3$ µm in length (Yu and Malenka, 2003).

Description of Statistics Used to Model Branching Patterns.

To model the branching pattern differences between the various constructs, we used Poisson and Binomial generalized linear models (GLM; (McCullagh and Nelder, 1999). The number of primary dendrites is assumed to come from a Poisson distribution with a mean primary dendrites number that varies from construct to construct. We attempted to simplify the model by restricting the mean to be equal for a subset of constructs, i.e. group A (GFP and GFP-snapin(1-68)-GFP) and group B (GFP-snapin, GFP-snapin(69-end) and GFP-snapin(81-126)). We performed an all-subset selection, examining all possible combinations of constructs for which we can estimate a common mean. The final model was selected via minimum BIC (Bayesian Information Criterion; (Schwarz, 1978). We checked the goodness of fit of the Poisson model (p-value=0.99), and saw no clear violations of this model assumption.

To examine the proportion of primary dendrites that branch, we used a Binomial generalized linear model. We checked the goodness of fit of the Binomial model (Chi-square goodness of fit test, p-value 0.15), and saw no consistently clear deviations from the assumed model. Following standard practice of Binomial GLMs, we related the branching proportion to the log of number of primary dendrites via a logit transform. We performed an all-subset selection, examining all possible combinations of constructs for which we can estimate a set of parameters in the Binomial model. The best model, selected by BIC, is one that states that only two distinct distributions are needed: group A (GFP and snapin(1-68)) and group B (snapin(69-end) and snapin(81-126)). Thus, the snapin, snapin(69-end) and snapin(81-126) constructs lead to an increase in branching proportion that cannot be explained by the decrease in primaries alone. We also analyze the number of secondary dendrites that stem from each primary. We detected no significant differences between any of the constructs. Almost all branching events are bifurcations.

Figure 8:
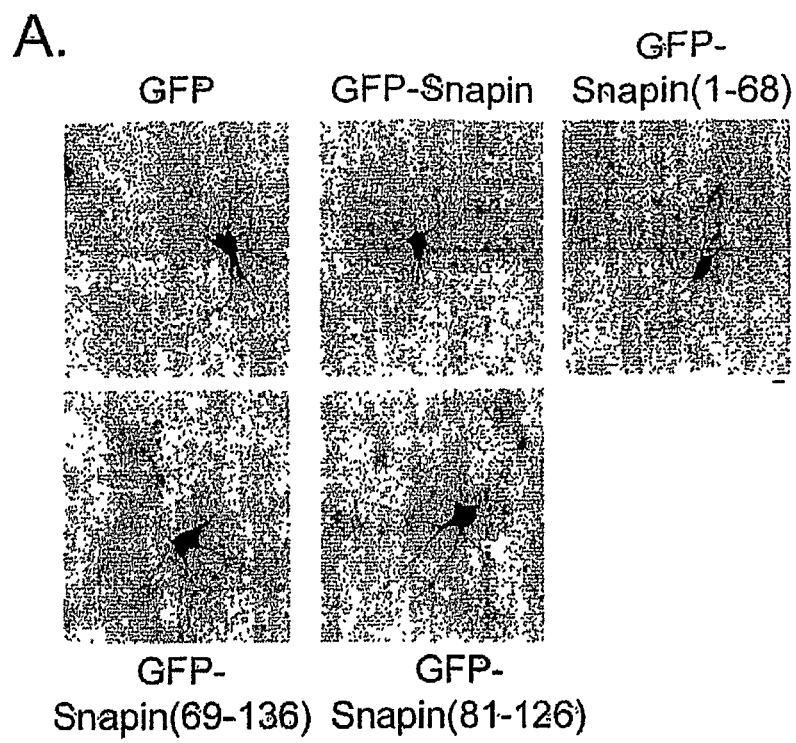
FIG. 8 illustrates the results of experiments demonstrating that overexpression of snapin results in changes in dendrite branching in hippocampal neurons.
Figure 8:
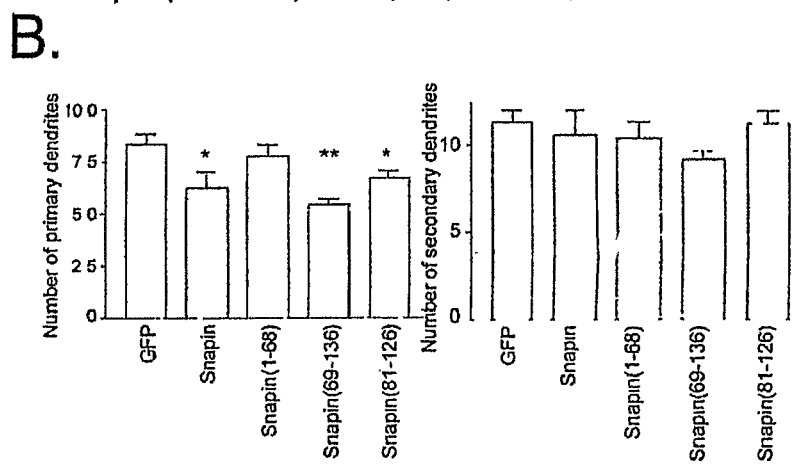
Figure 8:
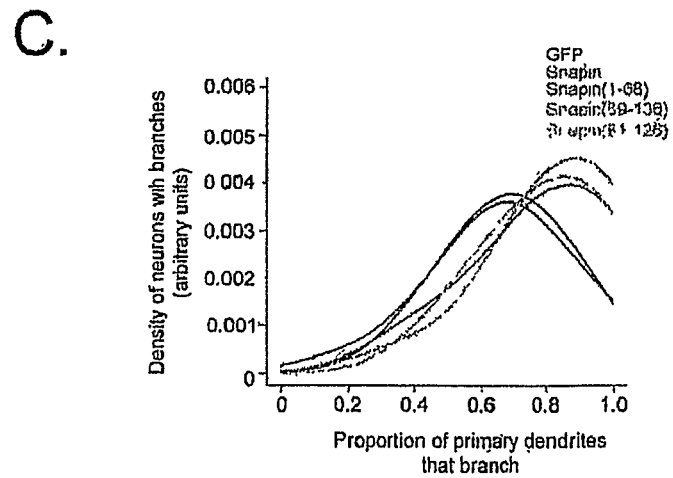

To assess how snapin's modulation of microtubule assembly may affect dendrite morphology, we overexpressed GFP-snapin, GFP-snapin(1-68), GFP-snapin(69-136), GFP-snapin(81-126), or GFP in hippocampal neurons beginning at 10 d.i.v. We then counted primary and secondary dendrites at 12 d.i.v. Overexpression of full length but not the N-terminal half (1-68) of snapin resulted in decreased primary dendrite number (FIGS. 8A and 8B). In addition, overexpression of the second half (69-136) and the minimal cypin binding region (81-126) also decreased primary dendrite number. Interestingly, none of the snapin proteins had an effect on secondary dendrite number (FIG. 8B), thereby increasing the probability of primary dendrite branching (FIG. 8C). This means that the number of dendrites that protrude from the cell body (or primary dendrites) is decreased by snapin; however, each of these individual dendrites is more likely to branch, resulting in more secondary dendrites. Compared to neurons expressing GFP alone, neurons overexpressing snapin have a decreased number of primary dendrites while secondary dendrite numbers stay the same. This indicates an increase in the probability of secondary branching when snapin is overexpressed. (FIG. 8C). To illustrate this point, we graphed the non-parametric estimate of the distribution of the branching probability. The graph clearly indicates that the branching probability is higher for GFP-snapin, GFP-snapin(69-136), and GFP-snapin(81-126) compared to GFP-snapin(1-68) and GFP as seen in FIG. 8C. Furthermore, average dendrite length was unaffected by overexpression of snapin (p=6.4196). Thus, our data suggest that snapin affects dendrite patterning by decreasing the number of primary dendrites and increasing the probability of dendrite branching.

It is important to note that the GFP, GFP-snapin, and GFP-snapin(81-126) constructs express at similar levels (p>0.05 by ANOVA followed by Bonferroni Multiple Comparisons Test; total fluorescence intensities are as follows: GFP=3551.14±77.81; GFP-snapin=3216.15±119.08; GFP-snapin(81-126)=3351.96±102.05). GFP-snapin(1-68) and GFP-snapin(69-136) express at lower levels than GFP (p<0.01; total fluorescence intensities are as follows: GFP-snapin(1-68)=2673.26±164.82 and GFP-snapin(69-136)=2447.71±112.19); however, this is not an issue since GFP-snapin(69-136) affects branching in a way consistent with the other constructs.

Example 9

Phosphorylation of Snapin Decreases its Binding to Cypin

Figure 9:
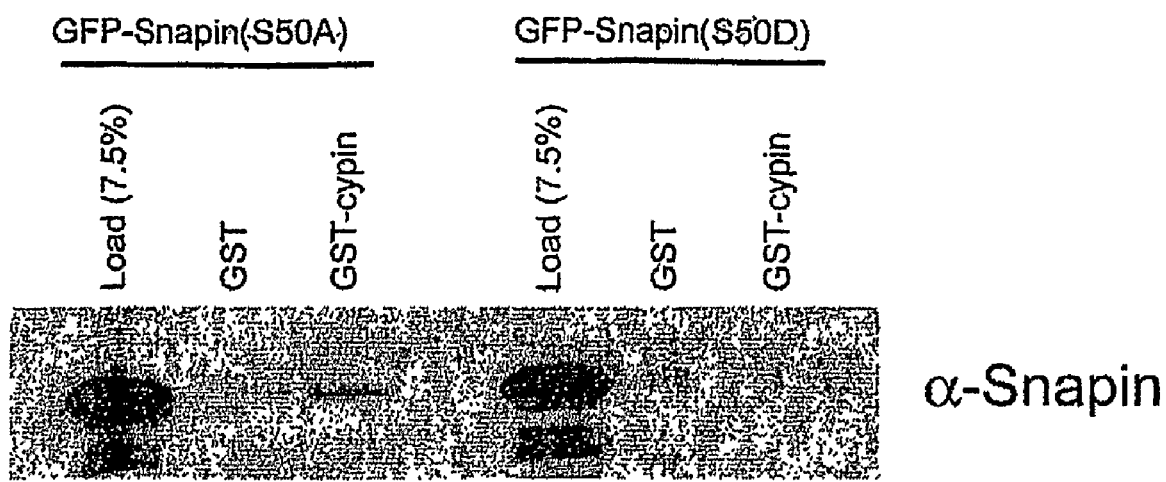
FIG. 9 illustrates that phosphorylation of snapin decreases binding to cypin.

Phosphorylation of snapin by PKA strengthens its association with SNAP-25 (Chheda et al., 2001). To address whether phosphorylation can play a role in regulating snapin's interaction with cypin, we expressed point mutants of snapin that mimic the constitutively unphosphorylated form (S50A) or the phosphorylated form (S50D). As seen in FIG. 9, only the unphosphorylated form binds to cypin over background levels (i.e. binding to GST). These data support the idea that phosphorylation of snapin negatively regulates its association with cypin.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An isolated peptide consisting of the amino acids 50-136 of the amino acid sequence of SEQ ID NO: 1, wherein the isolated peptide binds to a peptide comprising an amino acid sequence of SEQ ID NO: 4.

2. An isolated peptide consisting of the amino acid sequence of SEQ ID NO: 3, wherein the isolated peptide binds to a peptide comprising an amino acid sequence of SEQ ID NO: 4.

3. An isolated peptide consisting of the amino acid sequence of SEQ ID NO: 2, wherein the isolated peptide binds to a peptide comprising an amino acid sequence of SEQ ID NO: 4.

4. A screening method for identifying a microtubule assembly inhibiting compound, the method comprising:

obtaining at least one test sample and at least one control sample, wherein the at least one test sample and the at least one control sample comprise:

1) a snapin of SEQ ID NO: 1 or a fragment thereof comprising SEQ ID NO: 2, and 2) a cypin or a fragment thereof comprising SEQ ID NO: 4;

adding a compound to be tested for the microtubule inhibiting activity to the at least one test sample;

measuring in the at least one test sample and the at least one control sample an amount of binding of the snapin or the fragment thereof to the cypin or the fragment thereof, whereby a microtubule assembly inhibiting compound is identified by a measurement of an increase in the amount of binding of the snapin or the fragment thereof to the cypin or the fragment thereof in the at least one test sample as compared to the amount of binding in the at least one control sample.

5. The method of claim 4, further comprising adding at least a portion of tubulin to the at least one test sample and at least one control sample.

6. The method of claim 5, wherein the amount of binding of the snapin or the fragment thereof to the cypin or the fragment thereof is measured by measuring at least one parameter selected from the group consisting of:
 a) an amount of a complex between at least the cypin or a fragment thereof and the snapin or a fragment thereof,
 b) an amount of the snapin or a fragment thereof not bound to the cypin or a fragment thereof,
 c) an amount of the cypin or a fragment thereof not bound to the snapin or a fragment thereof,
 d) an amount of a complex between the cypin or a fragment thereof and at least the portion of tubulin,
 e) an amount of at least the portion of tubulin not bound to the cypin or a fragment thereof, and
 any combination of a) through e).

7. The method of claim 4, wherein the fragment of snapin is selected from the group consisting of:
 (a) a peptide consisting of the amino acid sequence of SEQ ID No: 2
 (b) a peptide consisting of the amino acid sequence of SEQ ID No: 3
 (c) a peptide comprising the amino acid sequence of SEQ ID No: 2,
 (d) a peptide consisting of amino acids 50-136 of SEQ ID NO: 1 and
 (e) any combination thereof.

8. The method of claim 4, wherein the fragment of cypin is a peptide consisting of the amino acid sequence of SEQ ID No: 4.

9. The method claim 4, wherein the sample is a cell-free system.

10. The method of any of the claim 4, wherein the sample comprises at least one cell.

11. The method of claim 4, wherein the sample comprises at least one neuron.

* * * * *

SEQUENCE LISTING

```
<160> NUMBER OF SEQ ID NOS: 4

<210> SEQ ID NO 1
<211> LENGTH: 136
<212> TYPE: PRT
<213> ORGANISM: Homo sapiens

<400> SEQUENCE: 1

Met Ala Gly Ala Gly Ser Ala Ala Val Ser Gly Ala Gly Thr Pro Val
 1               5                  10                  15

Ala Gly Pro Thr Gly Arg Asp Leu Phe Ala Glu Gly Leu Leu Glu Phe
            20                  25                  30

Leu Arg Pro Ala Val Gln Gln Leu Asp Ser His Val His Ala Val Arg
        35                  40                  45

Glu Ser Gln Val Glu Leu Arg Glu Gln Ile Asp Asn Leu Ala Thr Glu
    50                  55                  60

Leu Cys Arg Ile Asn Glu Asp Gln Lys Val Ala Leu Asp Leu Asp Pro
65                  70                  75                  80

Tyr Val Lys Lys Leu Leu Asn Ala Arg Arg Val Val Leu Val Asn
                85                  90                  95

Asn Ile Leu Gln Asn Ala Gln Glu Arg Leu Arg Arg Leu Asn His Ser
            100                 105                 110

Val Ala Lys Glu Thr Ala Arg Arg Ala Met Leu Asp Ser Gly Ile
        115                 120                 125

Tyr Pro Pro Gly Ser Pro Gly Lys
    130                 135

<210> SEQ ID NO 2
<211> LENGTH: 46
```

```
<212> TYPE: PRT
<213> ORGANISM: Homo sapiens

<400> SEQUENCE: 2

Tyr Val Lys Lys Leu Leu Asn Ala Arg Arg Arg Val Val Leu Val Asn
 1               5                  10                  15

Asn Ile Leu Gln Asn Ala Gln Glu Arg Leu Arg Arg Leu Asn His Ser
                20                  25                  30

Val Ala Lys Glu Thr Ala Arg Arg Arg Ala Met Leu Asp Ser
            35                  40                  45

<210> SEQ ID NO 3
<211> LENGTH: 68
<212> TYPE: PRT
<213> ORGANISM: Homo sapiens

<400> SEQUENCE: 3

Asn Glu Asp Gln Lys Val Ala Leu Asp Leu Asp Pro Tyr Val Lys Lys
 1               5                  10                  15

Leu Leu Asn Ala Arg Arg Arg Val Val Leu Val Asn Asn Ile Leu Gln
                20                  25                  30

Asn Ala Gln Glu Arg Leu Arg Arg Leu Asn His Ser Val Ala Lys Glu
            35                  40                  45

Thr Ala Arg Arg Arg Ala Met Leu Asp Ser Gly Ile Tyr Pro Pro Gly
        50                  55                  60

Ser Pro Gly Lys
 65

<210> SEQ ID NO 4
<211> LENGTH: 54
<212> TYPE: PRT
<213> ORGANISM: Homo sapiens

<400> SEQUENCE: 4

Ser Asn Ile Leu Leu Ile Asn Lys Val Asn Glu Lys Ser Leu Thr Leu
 1               5                  10                  15

Lys Glu Val Phe Arg Leu Ala Thr Leu Gly Gly Ser Gln Ala Leu Gly
                20                  25                  30

Leu Asp Gly Glu Ile Gly Asn Phe Glu Val Gly Lys Glu Phe Asp Ala
            35                  40                  45

Ile Leu Ile Asn Pro Lys
        50
```